United States Patent [19]
Van Assche et al.

[11] Patent Number: 5,917,126
[45] Date of Patent: *Jun. 29, 1999

[54] SACCHAROSE PHOSPHATE SYNTHETASE (SPS), A PREPARATION METHOD AND CDNA THEREFOR, AND USE OF THE CDNA FOR MODIFYING SPS EXPRESSION IN PLANT CELLS

[75] Inventors: Charles Van Assche, Marseille; Danielle Lando; Jean Michel Bruneau, both of Paris, all of France; Toni Alois Voelker, Davis, Calif.; Monica Gervais, Saint-Leu-la-Foret, France

[73] Assignee: Roussel Uclaf, France

[ * ] Notice: This patent is subject to a terminal disclaimer.

[21] Appl. No.: 08/429,054

[22] Filed: Apr. 26, 1995

Related U.S. Application Data

[62] Division of application No. 08/376,764, Jan. 23, 1995, which is a continuation of application No. 07/842,337, filed as application No. PCT/FR91/00593, Jul. 18, 1991.

[30] Foreign Application Priority Data

Jul. 20, 1990 [FR] France .................................. 90 402084

[51] Int. Cl.⁶ ............................... A01H 5/00; A01H 5/10; C12N 15/29; C12N 15/82
[52] U.S. Cl. ........................ 800/205; 800/250; 435/69.1; 435/172.3; 435/240.4; 435/320.1; 536/23.6
[58] Field of Search ............................... 435/320.1, 240.4, 435/172.3, 69.1; 800/205, 250; 536/23.6; 530/376

[56] References Cited

U.S. PATENT DOCUMENTS 5,387,756   2/1995   Burrell et al. ........................... 800/205

OTHER PUBLICATIONS

Kerr et al 1987 Planta 170:515–519.
Salerno et al 1991 Physiologia Plantarum 81:541–547.
Nguyen–Quoc et al 1990 Plant Physiol 94:516–523.
Dickinsen et al 1991 Plant Physiol 95:420–425.
Von Schaewen et al 1990 The EMBO Journal 9 (10):3033–3044.
Worrell et al 1991 (Oct.) The Plant Cell 3:1121–1130.
Shewmaker et al 1992 Plant Physiol 100:1083–1086.
Sonnewald et al 1992 Plant Physiol 99:1267–1270.
Huber et al 1992 Plant Physiol 99:1275–1278.
Sonnewald et al 1993 Planta 189:174–181.
Klein et al 1993 Planta 190:498–510.
Werr et al 1985 The EMBO Journal 4 (6):1373–1380.

*Primary Examiner*—David T. Fox
*Attorney, Agent, or Firm*—Bierman, Muserlian and Lucas LLP

[57] ABSTRACT

A cDNA coating for a protein having saccharose phosphate synthetase activity and a vector permitting the expression of a protein having saccharose phosphate synthetase activity under the control of a promoter directing the said expression.

6 Claims, 16 Drawing Sheets

SPS 90 kd PEPTIDES

A8   ThrTrpIleLys (SEQ. ID NO.: 1)

B4   TyrValValGluLeuAlaArg (SEQ. ID NO.: 2)

B11  SerMetProProIleTrpAlaGluValMetArg (SEQ. ID NO.: 3)

SPS 30 kd PEPTIDES

4K   LeuArgProAspGlnAspTyrLeuMetHisIleSerHisArg (SEQ. ID NO.: 4)

12N  TrpSerHisAspGlyAlaArg (SEQ. ID NO.: 5)

SPS cDNA sequence

EcoRI
1 GAATTCCGGCGTGGGCGCTGGGCTAGTGCTCCCGCAGCGAGCGATCTGAGAGAACGGTAGAGTTCCGGC 69
  2

BamHI
70 CGGGCGCGCGGGAGAGAGGAGGGTCGGGGGAGGATCCGATGGCCGGAACGAGTGGATCAATGGG 138
                                     METAlaGlyAsnGluTrpIleAsnGly
                                     106

KpnI
139 TACCTGGAGGCGATCCTCGACAGCCACACCTCGTCGGGGTGCCGGCGGGCGGCGGGGGGAC 207
    TyrLeuGluAlaIleLeuAspSerHisThrSerSerArgGlyAlaGlyLyGlyLyGlyLyGlyAsp
    142

208 CCCAGGTCGCCGACGAAGGCGGCGAGCCCCGCGGCGCACATGAACTTCAACCCCTCGCCACTACTTC 276
    ProArgSerProThrLysAlaAlaSerProArgGlyAlaHisMETAsnPheAsnProSerHisTyrPhe

SalI
277 GTCGAGGAGGTGGTCAAGGGCGTCGACGAGAGCGACCTCCACCGGACGTGGATCAAGGTCGTCGCCACC 345
    ValGluGluValValLysGlyValAspGluSerAspLeuHisArgThrTrpIleLysValValAlaThr
                                299                                A8

FIG. 7A

```
           XhoI
           |
346  CGCAACGCCCCGAGGCGCAGCACCAGGCTCGAGAACATGTGCTGGCGGATCTGGCACCTCGGCGCAAG    414
     ArgAsnAlaArgGluArgSerThrArgLeuGluAsnMETCysTrpArgIleTrpHisLeuAlaArgLys
                                         374

415  AAGAAGCAGCTGGAGCTGGAGGGCATCCAGAGAATCTCGGCCAAGAAGGAAGCAGGAGCAGGTGCGT    483
     LysLysGlnLeuGluLeuGluGlyIleGlnArgIleSerAlaArgLysGluGlnGluGlnValArg

484  CGTGAGGCGACGGAGGACCTGGCCGAGGATCTGTCAGAAGGGCGAGAAGGGAGACACCATCGGCGAGCTT    552
     ArgGluAlaThrGluAspLeuAlaGluAspLeuSerGluGlyGluLysGlyGluHisThrIleGlyGluLeu

553  GCGCCGGTTGAGACGACCAAGAAGAAGTTCCAGAGAACTTCTGACCTTACCGTCTGTCTGACGAC    621
     AlaProValGluThrThrLysLysLysPheGlnArgAsnPheSerAspLeuThrValTrpSerAspAsp

HindIII
          |
622  AATAAGGAGAAGAAGCTTTACATTGTGCTCATCAGGGTGCATGGTCTCTTGTTCGTGGAGAAAACATGGAA    690
     AsnLysGluLysLysLeuTyrIleValLeuIleSerValHisGlyLeuValLeuArgGlyValGluAsnMETGlu
                                 635

691  CTAGGTCGTGATTCTGATACAGGTGGCCAGGTGAAATATGTGGTCGAACTTGCAAGAGCGATGTCAATG    759
     LeuGlyArgAspSerAspThrGlyGlyGlnValLysTyrValValLysTyrValValValGluLeuAlaArgAlaMETSerMET
                                                                    B4

760  ATGCCTGGAGTGTACAGGGTGGACCTCTTCACTCGTCAAGTGTCATCTCCTGACGTGGACTGGAGCTAC    828
     METProGlyValTyrArgValAspLeuPheThrArgGlnValSerSerProAspValAspTrpSerTyr
```

FIG. 7B

```
829  GGTGAGCCAACCGAGATGTTATGCGCCGGTTCCAATGATGGAGAGGGGATGGGTGAGAGTGGGCGGAGCC  897
     GlyGluProThrGluMETLeuCysAlaGlySerAsnAspGlyGluGlyMETGlyGluSerGlyGlyAla

898  TACATTGTGCGCATACCGTGTGGGCCGCGGGATAAATACCTCAAGAAGGAAGCGTTGTGCCTTACCTC   966
     TyrIleValArgIleProCysGlyArgAspLysTyrLeuLysLysGluAlaLeuTrpProTyrLeu

967  CAAGAGTTTGTCGATGGAGCCCTTGCGCATATCCTGAACATGTCCAAGGCTCTGGGAGAGCAGGTTGGA 1035
     GlnGluPheValAspGlyAlaLeuAlaHisIleLeuAsnMETSerLysAlaLeuGlyGluGlnValGly

1036 AATGGGAGGCCAGTACTGCCTTACGTGATACATGGGCACTGGCCACTGGGAGGAACAAGCTGGAACAA  1104
     AsnGlyArgProValLeuProTyrValIleHisGlyHisTrpProLeuGlyArgAsnLysLeuGluGln

1105 CTTTCTGGTGCGCTGAATGTGCCAATGGTGCTCACTGGCCACTCACTTGGGAGGAGATGTTGCTGCTC  1173
     LeuSerGlyAlaLeuAsnValProMETValLeuThrGlyHisSerLeuThrTrpGlyAspValAlaAlaLeu

1174 CTGCTGAAGCAAGGGCGCATGTCCAAGGAGGAGATCGATTCGACATACAAGATCATGAGGCGTATCGAG 1242
     LeuLeuLysGlnGlyArgMETSerLysGluGluIleAspSerThrTyrLysIleMETArgArgIleGlu

1243 GGTGAGGAGCTGGCCCTGGATGCGTCAGAGCTTGTAATCACGAGCACAAGGCAGGAGATTGATGAGCAG 1311
     GlyGluGluLeuAlaLeuAspAlaSerGluLeuValIleThrSerThrArgGlnGluIleAspGluGln

1312 TGGGGATTGTACGATGGATTTGATGTCAAGCTTGAGAAAGTGCTGAGGGCACGGGCCGAGGGCCGGGTT 1380
     TrpGlyLeuTyrAspGlyPheAspValLysLeuGluLysValLeuArgAlaArgAlaArgGlyVal
                                    HindIII
                                    1340
```

```
      NcoI
       |
1381  AGCTGCCATGGTCGTTACATGCCTAGGATGGTGGTGATTCCTCCGGAATGGATTTCAGCAATGTTGTA  1449
      SerCysHisGlyArgTyrMETProArgMETValValIleProProGlyMETAspPheSerAsnValVal
                              1387

1450  GTTCATGAAGACATTGATGGGGATGGTGACGTCAAAGATGATATCGTTGGTTTGGAGGGTGCCTCACCC  1518
      ValHisGluAspIleAspGlyAspGlyAspValLysAspAspIleValGlyLeuGluGlyAlaSerPro

1519  AAGTCAATGCCCCAATTTGGGCCGAAGTGATGCGGTTCCTGACCAACCCTCACAAGCCGATGATCCTG  1587
      LysSerMETProProIleTrpAlaGluValMETArgPheLeuThrAsnProHisLysProMETIleLeu
                             B11

1588  GCGTTATCAAGACCAGACCCGAAGAAGAACATCACTACCCTCGTCAAAGCGTTTGGAGAGTGTCGTCCA  1656
      AlaLeuSerArgProAspProLysLysAsnIleThrThrLeuValLysAlaPheGlyGluCysArgPro

1657  CTCAGGGAACTTGCAAACCTTACTCTGATCATGGGTAACAGAGATGACATCGACGACATGTCTCTGGC  1725
      LeuArgGluLeuAlaAsnLeuThrLeuIleMETGlyAsnArgAspAspIleAspAspMETSerAlaGly

1726  AATGCCAGTGTCCTCACCACAGTTCTGAAGCTGATTGACAAGTATGATCTGTACGGAAGCGTGGCGTTC  1794
      AsnAlaSerValLeuThrThrValLeuLysLeuIleAspLysTyrAspLeuTyrGlySerValAlaPhe
                                                           BglII
                                                            |
1795  CCTAAGCATCACAATCAGGCTGACGTCCCGGAGATCTATCGCCTCGGGGCCAAAATGAAGGGCGTCTTC  1863
      ProLysHisHisAsnGlnAlaAspValProGluIleTyrArgLeuAlaLeuAlaLysMETLysGlyValPhe
                                              1827

1864  ATCAACCCTGCTCGTTGAGCCGTTTGGTCTCCACCCTGATCGAGGCTGCGGGCACACGGACTCCGATA  1932
      IleAsnProAlaLeuValGluProPheGlyLeuThrLeuIleGluAlaAlaHisGlyLeuProIle
```

```
                     SalI
                      |
1933 GTCGCTACCAAGAATGGTGGTCCGGTCGACATTACAAATGCATTAAACAACGGACTGCTGCTGTTGACCCA 2001
     ValAlaThrLysAsnGlyGlyProValAspIleThrAsnAlaLeuAsnAsnGlyLeuLeuValAspPro
                                    1958
                                                HindIII
                                                  |
2002 CACGACCAGAACGCCATCGCTGATGCACTGCTGAAGCTTGTGGCAGACAAGAACCTGTGGCAGGAATGC 2070
     HisAspGlnAsnAlaIleAlaAspAlaLeuLeuLysLeuValAlaAspLysAsnLeuTrpGlnGluCys
                                         2036

2071 CGGAGAAACGGGCTGCGCAACATCCACCTCTACTACTCCATGGCCGGAGCACTGCCGACTTACCTCACCAGG 2139
     ArgArgAsnGlyLeuArgAsnIleHisLeuTyrSerTrpProGluHisCysArgThrTyrLeuThrArg

2140 GTGGCCGGGTGCCGGTTAAGGAACCCGAGGTGGCTGAAGGACACACCAGCAGATGCCGAGCCGATGAG 2208
     ValAlaGlyCysArgLeuArgAsnProArgTrpLeuLysAspThrProAlaAspAlaGlyAlaAspGlu
                NcoI
                 |
2209 GAGGAGTTCCTGGAGGATTCCATGGACGCTCAGGACCTGTCACTCCGTCTGTCCATCGACGGTGAGAAG 2277
     GluGluPheLeuGluAspSerMETAspAlaGlnAspLeuSerLeuArgLeuSerIleAspGlyGluLys
                                         2229

2278 AGCTCGCTGAACACTAACGATCCACTGTGGTTCGACCCCCAGGATCAAGTGCAGAAGATCATGAACAAC 2346
     SerSerLeuAsnThrAsnAspProLeuTrpPheAspProGlnAspGlnValGlnLysIleMETAsnAsn

2347 ATCAAGCAGTCGCTCAGCGCCTTCCTCCGTCAGTGCCAGGCCGAGGGCACAGGCAGCACCATG 2415
     IleLysGlnSerSerAlaLeuProProSerMETSerSerValAlaAlaGluGlyThrGlySerThrMET
```

FIG. 7E

```
2416 AACAAATACCCACTCCTGCGCCGGCGCCCGGCGCTTGTTCGTCATAGCTGTGTGACTGCTACCAGGAGAT  2484
     AsnLysTyrProLeuLeuArgArgArgArgLeuPheValIleAlaValAspCysTyrGlnAspAsp
                                                          PstI

2485 GGCCGTGCTAGCAAGAAGATGCTGCAGGTGATCCAGGAAGTTTCAGAGCAGTCCGATCGGACTCCCAG  2553
     GlyArgAlaSerLysLysMETLeuGlnValIleGlnGluValPheArgAlaValArgSerAspSerGln
                           BglII                 SalI                PstI

2554 ATGTTCAAGATCTCAGGGTTCACGCTGTCGACTGCCATGCCGTTGTCCGAGACACTCCAGCTTCTGCAG  2622
     METPheLysIleSerGlyPheThrLeuSerThrAlaMETProLeuSerGluThrLeuGlnLeuLeuGln
                                                                   2622

2623 CTCGGCAAGATCCCAGCGACCGACTTCGACGCCCTCATCTGTGGCAGCGGCGAGGTGTACTATCCT  2691
     LeuGlyLysIleProAlaThrAspPheAspAlaLeuIleCysGlySerGlyGluValTyrTyrPro

2692 GGCACGGGCGAACTGCATGGACGCTGAAGGAAAGCTGAAGCTGCGCCAGATCAGGACTATCTGATGCACATCAGC  2760
     GlyThrAlaAsnCysMETAspAlaGluGlyLysLeuArgProAspGlnAspTyrLeuMETHisIleSer
                                                                    4K

2761 CACCGCTGGTCCCATGACGGCGAGGCAGACCATAGCGAAGCTCATGGGCGCTCAGGACGGGTTCAGGC  2829
     HisArgTrpSerHisAspGlyAlaArgGlnThrIleAlaLysLeuMETGlyAlaGlnAspGlySerGly
     ================================================================
                                12N
```

FIG. 7F

2830 GACGCTGTCGAGCAGGACGTGGCCGTTCCAGTAATGCACACTGTGTCGCGTTCCTCATCAAAGACCCCCAA 2898
     AspAlaValGluGlnAspValAlaSerSerAsnAlaHisCysValAlaPheLeuIleLysAspProGln

2899 AAGGTGAAAACGGTCGATGAGATGAGGAGCGGCTGAGGATGCGTGGTCTCCGCTGCCACATCATGTAC 2967
     LysValLysThrValAspGluMETArgSerGlyLeuArgCysHisIleMETTyr
                                                    PstI
                                                    |
2968 TGCAGGAACTCGACAAGGCTTCAGGTTGTCCCTCTGCTAGCATCAAGGTCACAGGTTCAGGTATCTT 3036
     CysArgAsnSerThrArgLeuGlnValValProLeuLeuAlaSerArgSerGlnAlaLeuArgTyrLeu
                                                              2972
                                                                        XbaI
                                                                        |
3037 TCCGTGCGCTGGGGCGTATCTGTGGGAACATGTATCTGATCACCGGGGAACATGGCAGACACCGATCTA 3105
     SerValArgTrpGlyValSerValGlyAsnMETTyrLeuIleThrGlyGluHisGlyAspThrAspLeu
                                                                         3103

FIG. 7G

3106 GAGGAGATGCTATCCGGGCTACACAAGACCGTGATCGTCCGTGGCGTCACCGAGAAGGGTTCGGAAGCA 3174
     GluGluMETLeuSerGlyLeuHisLysThrValIleValArgGlyValThrGluLysGlySerGluAla

3175 CTGGTGAGGAGCCCAGGAAGCTACAAGAGGGACGATGTCGTCCCGTCTGAGACCCCCTTGGCTGCGTAC 3243
     LeuValArgSerProGlySerTyrLysArgAspAspValValProSerGluThrProLeuAlaAlaTyr

3244 ACGACTGGGTGAGCTGAAGGCCGACGAGATCATGCGGGCTCTGAAGCAAGTCTCCAAGACTTCCAGCGGC 3312
     ThrThrGlyGluLeuLysAlaAspGluIleMETArgAlaLeuLysGlnValSerLysThrSerSerGly

3313 ATGTGAATTTGATGCTTCTTTTACATTTGTCCCTTTTCTTCACTGCTATATAAAATAAGTTGTGAACAG 3381
     MET

3382 TACCGCGGGTGTGTATATATATATTGCAGTGACAAATAAAAACAGGACACTGCTAACTATACTGGTGAAT 3450

EcoRI
                                                                  |
3451 ATACGACTGTCAAGATTGTATGCTAAGTACTCCATTTCTCAATGTATCAATCGGAATTC 3509
                                                            3505

FIG. 7H (SEQ. ID NOS.: 11 AND 12)

SACCHAROSE PHOSPHATE SYNTHETASE (SPS), A PREPARATION METHOD AND CDNA THEREFOR, AND USE OF THE CDNA FOR MODIFYING SPS EXPRESSION IN PLANT CELLS

PRIOR APPLICATIONS

This application is a division of U.S. patent application Ser. No. 376,764 filed Jan. 23, 1995 which is a continuation of U.S. patent application Ser. No. 842,337 filed Mar. 20, 1992, now abandoned which is based on PCT application No. FR91/00593 with an international filing date of Jul. 18, 1991 claiming priority of French application Serial No. 90-402,084.9 filed Jul. 20, 1990.

SUMMARY OF THE INVENTION

The present invention relates to saccharose phosphate synthetase (SPS), its preparation process, its complementary DNA and the use of the latter to modify the rate of expression of SPS in vegetable cells.

A subject of the invention is proteins having the activity of saccharose phosphate synthetase (SPS).

By vegetable cell is meant all plant cells being able to form undifferentiated tissue such as calluses or differentiated tissues such as embryos, certain parts of plants, whole plants or also seeds.

By plant is meant notably plants producing seeds, for example the grasses such as straw cereals such as wheat, barley, maize or oats, the legumes such as soya, oleaginous plants such as sunflowers, plants with tubers such as potatoes, plants with roots such as beetroots or fruits such as tomatoes.

More particularly a subject of the invention is saccharose phosphate synthetase and notably the saccharose phosphate synthetase of plants.

By plants is meant for example the grasses such as for example wheat, barley, maize, sugar cane, vegetables such as tomatoes and soya, fruits, such as apples and bananas.

FIELD OF THE INVENTION

Saccharose phosphate synthetase is a key enzyme in the regulation mechanisms of saccharose, but also in the regulation mechanisms of the distribution of carbon between starch and saccharose in photosynthesis (see on this subject the article by Jack PREISS in TIBS January 1984, pages 24 and following, or also the article by Mark STITT and Coll. in Biochemistry of Plants vol. 10, 1987 pages 327 and following).

The SPS appears to be specific to the species concerned; Joan L—Walker and Steven C. Huber who have purified and carried out a preliminary characterization of the saccharose phosphate of spinach indicate clearly that the antibodies obtained recognize exclusively the SPS of spinach (cf PLANT PHYSIOL (1989) 89, 518–524).

More precisely a subject of the invention is the SPS of maize.

The SPS of maize can exist in a pure or practically pure form.

More precisely a subject of the invention is the proteins defined previously of molecular weight of the order of 110 to 130 kD appearing in the monomer, dimer or tetramer form and their derivatives having at least one peptide whose amine acid sequence is the following:

ThrTrpIleLys (SEQ ID NO:1)
TyrValValGluLeuAlaArg (SEQ ID NO:2)
SerMetProProIleTrpAlaGluValMetArg (SEQ ID NO:3)
LeuArgProAspGlnAspTyrLeuMetHisIleSerHisArg (SEQ ID NO:4)
TrpSerHisAspGlyAlaArg (SEQ ID NO:5)

Notably a subject of the invention is the proteins defined previously having the amino acid sequence described in FIG. 7 (SEQ ID NO:11).

Also a subject of the invention is the derivatives of the proteins defined previously modified by genetic engineering techniques and presenting the activity of the SPS.

Also a subject of the invention is a preparation process characterized in that:
a) an extract is made from parts of the plants preserved at low temperature by grinding, centrifugation and filtration,
b) the extract obtained is enriched in SPS protein by precipitation in an appropriate solvent, centrifugation and solubilisation of the precipitate obtained in a buffer solution,
c) the active protein thus obtained is purified by chromatography and if desired,
d) the hybridomas and monoclonal antibodies are prepared from an antigen solution obtained from one of the preparations obtained in paragraphs a), b), and c) above,
e) the hybridomas are screened and the monoclonal antibody or antibodies directed specifically against the SPS are selected,
f) the SPS obtained is purified by means of the antibodies prepared in this way.

More precisely a subject of the invention is a process characterized in that:
a) an extract is made from parts of maize plants preserved at low temperature by grinding, centrifugation and filtration,
b) the extract obtained is enriched in proteins by precipitation in polyethyleneglycol, centrifugation and solubilisation of the precipitate obtained in a buffer solution,
c) the SPS protein thus obtained is purified by low pressure anion exchange chromatography, then by chromatography on heparin Sepharose, then by high pressure anion exchange chromatography,
d) the active fractions are purified by passage through 2 high pressure chromatography columns, and, if desired,
e) the hybridomas and monoclonal antibodies are prepared from an antigen solution obtained from a preparation a), b), c),
f) the hybridomas are screened and the antibodies directed specifically against the SPS are selected,
g) the SPS obtained previously is purified by means of antibodies thus prepared.

In a preferred embodiment:
the maize used is a maize of PIONEER 3184 strain,
the parts of maize plants used are leaves preserved at low temperature for example between −50° C. and −90° C.,
the purification in polyethyleneglycol (PEG) takes place in two stages:
a first precipitation where the final concentration of PEG is close to 6%,
a second precipitation where the final concentration of PEG is close to 12%.
the various chromatographies are carried out as follows:
1st chromatography: DEAE Sepharose,
2nd chromatography: heparin Sepharose: it should be noted that the preparation thus obtained can be preserved for several days without major loss of activity,
3rd HPLC chromatography: Mono Q chromatography,
4th HPLC chromatography: hydroxylapatite, 5th HPLC chromatography: DEAE.

in the course of these various purification stages and the following, the measurement of the SPS activity is preferably carried out using two different methods:
a) a method based on a calorimetric test or a resorcinal test,
b) a method based on the determination of one of the products formed during the transformation reactions involving the SPS. These two methods are detailed in the experimental part set out hereafter.

mice are immunized with several injections of the purified enzymatic preparation.

Different mouse types can be used, for example BALB/C mice.

The antigen is used in the complete Freund adjuvant then in the incomplete Freund adjuvant.

Several injections of the antigen are administered to the mice: good results were obtained with three injections of mono Q fractions followed by three injections of final fractions (on days 0, 14, 27, 60, 90 and 105 for example).

The first injections are carried out by subcutaneous route, for example in the foot pads, the last injection is carried out by intravenous route in the tail for example.

the preparation of cellular suspensions of spleen thus immunized is treated in a clonic fashion.

The stages of fusion with myeloma cells, preservation of the hybridomas, cloning and production of the antibodies are achieved according to known methods.

To detect the hybridomas secreting the antibodies directed against the antigen, two methods are used to select the detection antibodies of the secreting hybridomas directed against the immunization antigen:

a method of detection of antibody inhibitors of SPS activity, a method of antibody activity directed against SPS activity.

These methods are preferably those described in the experimental part.

Also a subject of the invention is the cell lines of the hybridomas obtained and notably the cell lines of the following hybridomas:

SPA 2-2-3: I-971
SPA 2-2-22: I-970
SPA 2-2-25: I-972
SPB 3-2-19: I-973
SPB 5-2-10: I-974
SPB 5-4-2: I-975
SPB 13-1-7: I-976
SPB 13-2-2: I-977 which were deposited on 11th Jun. 1990 with the Collection Nationale de Culture de Microorganismes (CNCM—Institute Pasteur) under the numbers mentioned.

Also a subject of the invention is monoclonal antibodies directed specifically against the SPS.

Also a subject of the invention is a preparation process for proteins characterized in that a preparation containing said proteins is passed through a chromatography column containing the monoclonal antibodies directed specifically against said proteins and in this way the desired proteins are obtained. Also a subject of the invention is the DNA coding sequences for the proteins defined previously and notably the SPS of maize, whose sequence appears in FIG. 7.

The complementary DNA (cDNA) coding for the saccharose Phosphate Synthethase (SPS) enzyme was prepared as follows:

1—Sequencing of purified SPS peptide fragments.

Purified preparations of maize SPS obtained previously give, upon separation on acrylamide gel, a minor band of 120 kd (corresponding to the total protein sequence) and two major bands of 90 and 30 kd. These two polypeptides are separated by electrophoresis then electroelution. Trypsic digestion followed by the sequencing of fragments obtained allowed the amino acid sequences of 5 peptides to be determined (FIG. 3). Knowledge of the amino acid sequence of these peptides allows the corresponding nucleotide sequence to be determined.

2—Isolation of the RNA of maize leaves.

The total RNA is isolated according to the TURPEN and GRIFFITH method (1986, Biotechniques vol.4 pp 11–15).

The RNA polyA+ is prepared by passage through a column of oligodT cellulose according to known techniques.

3—Construction of a cDNA library.

The cDNA synthesis is carried out using the "PROMEGA"® synthesis kit. The reverse transcriptase of MMLV is used in place of AMV reverse transcriptase. The size of cDNA's obtained is comprised between 500 base pairs and several thousand base pairs. ECoRI adapters are added to the ends of the cDNA before cloning in a lambda gt11 expression vector. The cDNA library contains approximately $1.5 \times 10^6$ transformants.

4—The use of PCR for the synthesis of a specific nucleotide probe for SPS.

The oligonucleotides derivatised from B11 peptide sequences (coming from 30 kd) and 4 K (coming from 90 kd) described in FIG. 3 are used as initiators in PCR-type reactions. The starting hypothesis is that the polypeptides of 30 and 90 kd are the degradation products of the SPS protein of 120 kd. Therefore the peptides resulting from the SPS 30 and SPS 90 fragments have to come from the translation of the same RNA messenger. In this hypothesis the use of a pair of oligonucleotides corresponding to the peptide sequences in a PCR-type reaction has to result in the synthesis of a DNA fragment of determined size if these oligonucleotides are complementary to an indentical DNA sequence. Not knowing the respective position of these peptides in the SPS protein, the various combinations are tried out. Only the pair of CD3 oligonucleotides (FIG. 4) gives a DNA fragment of determined size (1200 base pairs).

5—Screening the cDNA library:

250,000 lambda gt11 transformants have been screened using the DNA fragment of 1200 base pairs obtained by PCR reaction (described previously). 16 positive clones have been obtained. The insertion sizes vary from 0.3 kb to 2.8 kb. The sequence obtained is not complete on the R' side. A second screening of the library using a DNA fragment of 400 bp corresponding to the 5' part of the SPS3 clone allows a clone (SPS 61) to be obtained which goes further in the 5' part (FIG. 6) without having the 5' terminus.

6—Production and screening of a second cDNA library allowing the cloning of the 5' part of the cDNA coding for the SPS.

An oligonucleotide complementary to the 5' sequence of the SPS61 clone is used as initiator for the synthesis of the cDNA. After synthesis of the second strand, the cDNA was cloned in the lambda phage. The library contains approximately 1 million clones. The SPS 90 and SPS 77 clones were obtained during the screening of this library with SPS 61 (FIG. 6). The sequence of these clones has allowed the region overlapping with the SPS 61 clone to be determined. The SPS 90 clone allows the 5' part of the SPS to be reached.

Verification of the organization of the different sequences (FIG. 6) allowing the complete cDNA sequence to be obtained was able to be carried out by using the PCR technique. The initiators used belong to the SPS 3 and SPS 90 clones. The obtaining of a fragment of 750 base pairs of the exact size predicted by the complete sequence permits the assertion that the SPS 3 and SPS 90 clones derive from the same RNA messenger.

7—Assembly of the complete cDNA.

Also a subject of the invention is the genomic DNA containing the coding part for the proteins defined previously and sequences necessary for the expression and regulation of this protein in plants.

Also a subject of the invention is a process for modifying the expression rate of the SPS in a plant, characterized in that the cells of said plant are transformed by means of an expression vector containing the cDNA defined previously.

Also a subject of the invention is a vector allowing the expression of the SPS protein under the control of a promoter capable of directing the expression and preferably the superexpression of said SPS in a plant cell and a 3' region containing transcription regulation signals for the expression of the gene coding for the SPS.

Moreover a subject of the invention is the plants obtained by the implementation of this process.

Also a subject of the invention is the seeds obtained.

BRIEF DESCRIPTION OF THE DRAWINGS

FIG. 3 shows peptide sequences derived from the SPS protein.

FIG. 4 shows oligonucleotides used for CD3 and CD4 PCR.

FIG. 7 shows the sequence of the SPS cDNA.

DETAILED DESCRIPTION OF THE INVENTION

Figure 1:
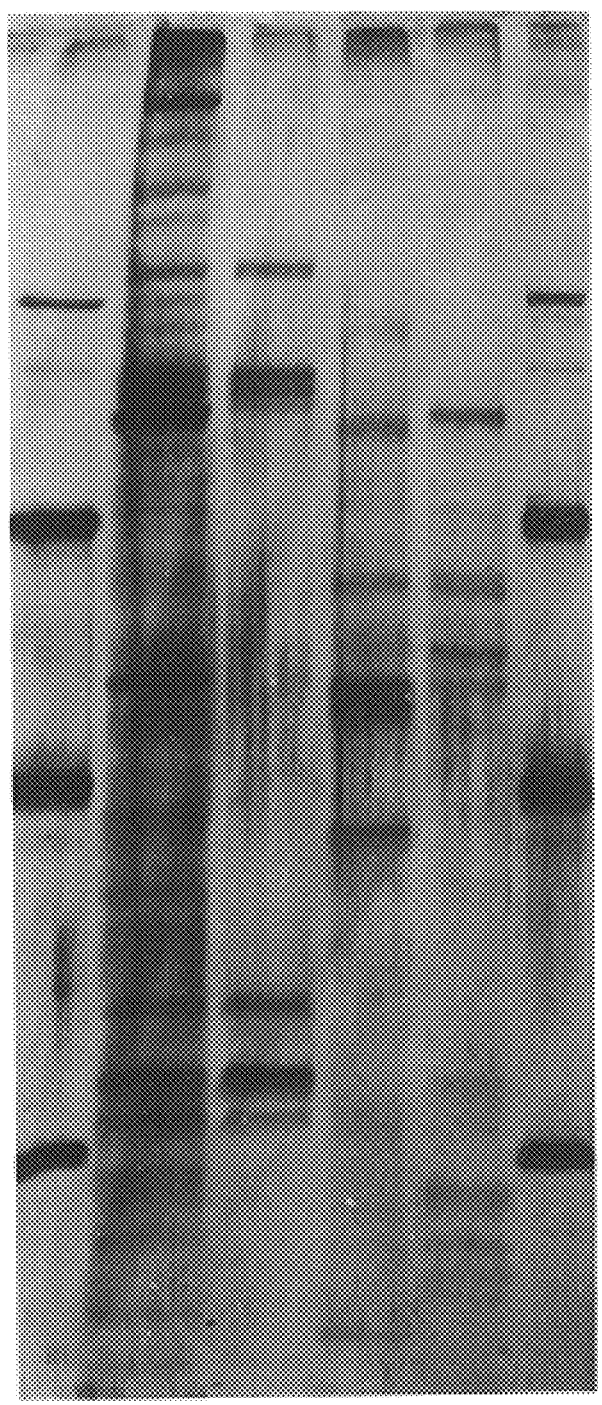
FIG. 1 shows the SDS-PAGE profile illustrating the purification of maize saccharose phosphate synthetase.

The following examples illustrate the invention without however limiting it.

1—PURIFICATION OF SACCHAROSE PHOSPHATE OF MAIZE 1.1—Determination Method of the Enzymatic Activity (SPS)

The monitoring of the SPS activity during purification is carried out in 2 ways:

a) either by means of a calorimetric test (P. S. Kerr et al., Planta 1987, 170: 515–519) so-called resorcinol test.

The saccharose Phosphate Synthetase or UDP glucose—D Fructose—Phosphate Glucosyltransferase catalyses the reaction:

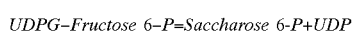
UDPG–Fructose 6–P=Saccharose 6-P+UDP

UDPG: Uridine Di-Phospho Glucose
Fructose 6-P or F6P: Fructose 6-Phosphate
Saccharose 6-P: Saccharose 6-Phosphate The saccharose 6-P formed reacts with the resorcinol to give a red-coloured compound quantifiable by spectrophotometry at 520 nm (D.O. 520 nm).

b) or by means of a paired enzymatic system (S. Harbron and al., Anal. Biochem. 1980, 107: 56–59) made up in the following manner:

UDPG+F6P<=>SACCHAROSE 6 P+UDP

SPS

UDP+ATP<=>ADP+UTP

Nucleoside Diphosphokinase NP$_2$K

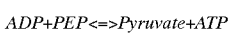
ADP+PEP<=>Pyruvate+ATP

Pyruvate kinase PK

pyruvate+NADH<=>NAD+lactate

Lactate dehydrogenase LDH

The disappearance of NADH at 340 nm is measured and 1 mol of NAD formed or 1 mol of NADH consumed corresponds to 1 mol of saccharose 6 P formed.

1.2—Purification of the SPS (Preparation of the Immunogen)

1.2.1—Extraction

The starting material for the purification is constituted by young maize leaves (Pioneer 3184 strain) cut up, de-veined, deep-frozen in liquid nitrogen and stored at −70° C.

250 g of leaves are suspended in 1 liter of HEPES buffer 50 mM MgCl$_2$ 10 mM EDTA 1 mM DTT 5 mM pH 7.5 (extraction buffer) with 11 g of Polyvinylpyrrolidone added, with nitrogen bubbled through it and cooling to 0° C.

The leaves are ground until a homogeneous suspension is obtained. This suspension is filtered. The resultant product is then centrifuged at 14000 g for 20 mn at 4° C.

While maintaining the bubbling through of nitrogen, a solution of 50% Poly Ethylene Glycol (PEG 8000 "Breox" 50% p/v in extraction buffer) is added to the supernatant until a final PEG concentration of 6% is reached. After centrifugation, 20 mn at 14000 g, 50% PEG is added to the supernatant until a final PEG concentration of 12% is reached. After centrifuging again, the supernatant is eliminated and the pellet is solubilised with 60 ml of HEPES buffer 50 mM, MgCl$_2$ 10 mM, EDTA 1 mM, DTT 5 mM, Ethylene Glycol (EG) 10%, KCl 0.08 M pH 7.5 (resuspension buffer). This solution is clarified by centrifuging 10 mn at 40000 g. The supernatant constitutes the final extract.

1.2.2—Low Pressure Anion Exchange Chromatography: DEAE Sepharose Fast-Flow Exchanger The final extract is chromatographed on a column of DEAE Sepharose Fast-Flow equilibrated in a resuspension buffer. After washing the column with the same buffer, the proteins adsorbed on the support are eluted by means of an increasing ionic strength of linear gradient between 0.08 M KCl and 0.35 M KCl in the HEPES buffer 50 mM, MgCl$_2$ 10 mM, EDTA 1 mM, DTT 5 mM, EG 10% pH 7.5 (buffer A). The flow rate applied during this experiment is 180 ml/h and chromatography is carried out at 4° C.

The SPS activity is eluted at approximately 0.17 M KCl.

1.2.3—Chromatography on Heparin Sepharose

The fractions containing the SPS activity are combined and diluted to ⅕th in buffer A then added to 12 ml Heparin Sepharose previously equilibrated in buffer A. After incubation for one hour with slow agitation at 4° C., the gel is washed with approximately 10 volumes of buffer A+0.05 M KCl then reconditioned in a chromatographic column.

The adsorbed proteins are eluted in an isocratic manner by means of a CAPS buffer 10 mM, $MgCl_2$ 10 mM, EDTA 1 mM, DTT 5 mM, EG 10%, Tween 80 0.01%, Heparin 1 mg/ml, Fructose 1%, KCl 0.25M pH 10 delivered at 60 ml/h. Chromatography is carried out at 4° C.

The fractions containing the SPS activity are combined (heparin fraction) and preserved on ice until the following purification stage. The enzyme at this stage is stable for at least a week.

The following purification stages are carried out using a High Performance Liquid Chromatography system (HPLC), and purification is monitored by means of a detector equipped with a filter allowing the ultra-violet absorption at 280 nm (A280) to be measured. The buffers and recovered fractions are maintained at low temperature.

1.2.4—High Performance Anion Exchange Chromatography: Mono Q

The heparin fraction is diluted to 2/3 in Triethanolamine buffer 20 mM, $MgCl_2$ 10 mM, EDTA 1 mM, DTT 10 mM, EG 3%, Tween 80 0.3% pH 7.5 (buffer A) and loaded onto an HPLC Mono Q HR10/10 column previously equilibrated with the same buffer with NaCl added (final concentration 0.18 M). After returning to 0 the proteins of the A280 adsorbed on the chromotographic support are eluted by means of a salt complex gradient made up as follows:

buffer A: cf above
buffer B: buffer A+NaCl 1 M

| time (minutes) | % B |
|---|---|
| 0 | 18 |
| 0.1 | 24 |
| 15 | 24 |
| 19 | 26 |
| 23 | 26 |
| 33 | 31 |
| 38 | 31 |
| 41 | 100 |
| 43 | 18 |

The flow rate applied on the column is 180 ml/h.

The SPS activity is eluted between 0.26 and 0.31 M NaCl. The active fractions are brought together (Mono Q fraction).

1.2.5—HPLC on Hydroxyapatite

The Mono Q FRACTION is loaded on an HPLC column of hydroxyapatite equilibrated with the buffer KH2PO4/K2HPO4 20 mM, EG 3%, Tween 80 0.3%, DTT 5 mM pH 7.5. After return to 0 the adsorbed proteins of the A280 are eluted by means of the following phosphate gradient:

buffer A: cf above
buffer B: idem buffer A but with 500 mM of K phosphate

| time (minutes) | % B |
|---|---|
| 0 | 2 |
| 5 | 11 |
| 9 | 13 |
| 14 | 13 |
| 29 | 40 |
| 31 | 100 |
| 32 | 100 |
| 35 | 2 |

The flow rate applied is 60 ml/h. It should be noted that at this stage the phosphate is a partial inhibitor of the SPS activity and it is therefore difficult to calculate a specific activity as well as a purification factor (cf table 1).

The SPS activity is eluted in these conditions with about 60 mM phosphate.

The above fractions are combined and constitute the HAC fraction.

1.2.6—HPLC on DEAE 5PW

The HAC fraction is loaded on a Di Ethyl Amino Ethyl (DEAE-5PW) type of anion exchange HPLC column previously equilibrated in a Triethanolamine buffer 20 mM, $MgCl_2$ 10 mM, EDTA 1 mM, EG 3%, DTT 2.5 mM, Betaine 2% pH 7.5 (Buffer A)+0.15 M NaCl.

After return to 0 the adsorbed proteins of the A280 are eluted by means of the following NaCl gradient:

buffer A: cf above
buffer B: idem buffer A with 1M NaCl

| time (minutes) | % B |
|---|---|
| 0 | 15 |
| 0.1 | 20 |
| 5 | 20 |
| 22 | 35 |
| 27 | 35 |
| 30 | 100 |
| 31 | 15 |

The flow rate used is 60 ml/h.

The SPS activity is eluted with approximately 0.3M NaCl.

1.2.7—Obtaining the Final Preparation: Concentration

The final preparation is concentrated by HPLC chromatography on Mono Q HR5/5 exchanger (5×50 mm, Pharmacia) and rapid elution.

The DEAE 5PW fraction (or the G200 fraction) is diluted to 2/3 in buffer A (idem 6) and loaded on the column which has been previously equilibrated with buffer A+0.18 M NaCl. The following gradient is then applied on the column:

buffers A & B: (idem 6)

| time (minutes) | % B |
|---|---|
| 0 | 18 |
| 10 | 40 |
| 12 | 100 |
| 13 | 18 |

The flow rate used is 60 ml/h.

The SPS activity is eluted with approximately 30% B (0.3 M NaCl).

The final preparation is stored at −20° C. until use.

Table 1 summarizes the results obtained at the different stages of purification in terms of the quantities of proteins and SPS activity.

TABLE 1

| | Protein concentration (mg/ml) | Volume (ml) | Sa** (U) | Pf** | Y* (%) |
|---|---|---|---|---|---|
| Homogenate | 1 | 1000 | 0.05 | 0 | 100 |
| Final extract | 4< <8 | 60 | 0.30 | 6 | 144 |
| DEAE FF frac. | 0.4< <.0.8 | 70 | 3 | 60 | 168 |
| Heparin frac. | 0.2< <0.4 | 25 | 9 | 180 | 90 |
| Mono Q frac. | (0.02) | 30 | — | — | — |

TABLE 1-continued

| | Protein concentration (mg/ml) | Volume (ml) | Sa** (U) | Pf** | Y* (%) |
|---|---|---|---|---|---|
| HAC frac. | (0.03) | 8 | — | — | — |
| Final prep. | 0.05 | 2 | 25 | 500 | 5 |

Key
Sa = Specific enzymatic activity: 1 U corresponds to 1 micromole of saccharose formed per minute per mg of protein at 37° C.
Pf = Purification factor
Y = Yield
() = approximate value
— = not determined
Remarks: ** the measurement of the quantity of proteins is carried out by using the Bradford method. The Tween interferes greatly in this method, it is not possible to determine the proteins and therefore to calculate an Sa at the level of stages containing it. In addition the phosphate being an inhibitor of the SPS activity, the determination during the HAC stage gives an underestimated result. * the increasing output during the first stages may be explained by the elimination during purification of some inhibitors of the SPS activity.

A profile (SDS—PAGE) illustrating the purification process and the quality of the final preparation is given in FIG. 1. The presence of 120, 95, and 35 Kd (Kilodaltons) proteins is correlated with the SPS activity.

Sequence studies of 35 and 95 Kd proteins carried out subsequently, seem to show that these proteins are probably degradation products of the 120 Kd protein. In addition, the antibodies directed against the 35 and 95 Kd proteins also recognize the 120 kd protein by immuno-detection after transfer onto a membrane, which demonstrates an antigen community between these three proteins (see further on). It must be pointed out, however, that adding protease inhibitors to the buffers during purification did not allow a 120 Kd protein to be obtained solely.

The saccharose phosphate synthetase seems therefore to be a di- or tetrameric protein having a 120 Kd protein (homo-dimer or homo-tetramer) as a base sub-unit.

Key to FIG. 1
The SDS—PAGE profile illustrating the purification of the maize saccharose phosphate synthetase: acrylamide gel at 8.5%, reducing conditons and staining with silver nitrate
M: Standard molecular weight B-Galactosidase (116 Kd), Bovine albumin (68 Kd), Ovalbumin (45 Kd), Carbonic anhydrase (29 Kd).
H: Heparin Fraction, 30 micrograms of proteins per well.
FP: Final Preparation, 7.5 micrograms of proteins per well.
FE: Final Extract, 7.5 micrograms of proteins per well.
D: DEAE Fast-Flow Fraction, 7.5 micrograms of proteins per well.

The protein bands which are visible at about 120 Kd (1), 95 Kd (2) and 35 Kd (3) are correlated, in the course of the chromatography stages, to the presence of an SPS activity in the fractions.

2—PREPARATION PROCESS FOR THE MONO-CLONAL ANTIBODIES DIRECTED AGAINST THE SACCHAROSE PHOSPHATE SYNTHETASE 2.1—Immunizations BALB/C mice are immunized by sub-cutaneous injection (pads and paws) according to the following methodology:

Day 0 Injection of approximately 5 micrograms of proteins (i.e. approximately 0.3 USPS per mouse): Mono Q pool emulsified volume for volume with Freund's Complete Adjuvant (FCA).

Day 14 Injection of approximately 5 micrograms of proteins (i.e. approximately 0.3 USPS per mouse: Mono Q pool emulsified volume for volume with Freund's Incomplete Adjuvant (FIA).

Day 27 Idem D14

Day 0+2 months Injection of approximately 20 micrograms of proteins: final preparation in FIA Day 0+3 months Injection of approximately 12 micrograms of proteins: final preparation in FIA Day 0+4.5 months Injection by intravenous route (IV) in the tail of approximately 20 micrograms of proteins: final pool as is.

Fusion is carried out 3 days after the IV immunization.

Serums are taken on D34, D67, D98 and D159 in order to measure the immune response (cf screening).

2.1.1—Screening Method

As the SPS used for the immunizations is not perfectly homogeneous, it is necessary to perfect a specific screening test for this enzyme. In fact an ELISA-type test also reveals antibodies directed against SPS non-related impurities which are present in the preparations having served as immunizations.

Two antibody detection methods are used:

detection method for antibody inhibitors of the SPS activity detection method for antibodies directed against the SPS (inhibitors or not).

a) Detection method for antibody inhibitors of the SPS activity

This screening method allows antibodies binding at the level of the SPS active site or at the level of a site close to it, to be detected and therefore preventing substrate access. In practice 70 μl of serum or supernatant of the hybridoma culture diluted in an appropriate manner is added to 70 μl of SPS preparation (Heparin fraction). After incubation for one hour at ambient temperature, the residual activity is determined using coupled enzymatic determination (Cf I-1). Results are expressed as a percentage of inhibition compared to the same SPS preparation treated in the same manner without antibodies.

b) Detection method for antibodies directed against the SPS (inhibitors or not)

This method is based on the precipitation of an antibody-SPS complex using a trainer system (mouse Ig anti-Ig coupled with Sepharose balls: Goat-anti mouse-Sepharose or GAM Sepharose). In practice 60 microliters of serum or supernatant of hybridoma culture diluted in an appropriate manner is added to 60 microliters of SPS preparation (Heparin fraction). After incubation for 2 hours at ambient temperature, the mixture is added to 50 microliters of GAM-SEPHAROSE at 25% washed 3 times beforehand with a HEPES buffer 50 mM, $MgCl_2$ 10 mM, EDTA 1 mM, EG 10%, DTT 5 mM pH 7.5. The mixture is incubated overnight at 4° C. under vibrational agitation. After centrifuging for 5 minutes at 3000 rpm the residual SPS activity in the supernatant is determined using coupled enzymatic determination (cf 1.1). The results are expressed as a precipitation percentage (% prec.) compared to the same SPS preparation treated in the same manner without antibodies.

2.1.2—Results 10 mice were immunized according to the protocol described above. The following table gives the results of precipitation determinations carried out with the heteroantisera of 10 mice on D159. The serums are diluted to 1/200.

| MOUSE | 1 | 2 | 3 | 4 | 5 | 6 | 7 | 8 | 9 | 10 |
|---|---|---|---|---|---|---|---|---|---|---|
| % PREC. | 45 | 22 | 32 | 64 | 36 | 30 | 22 | 16 | 39 | 37 |

Additional dilutions of the serum of mouse 4 gives the following results:

| DILUTION | % PRECIPITATION |
|---|---|
| 1/200 | 67 |
| 1/400 | 48 |
| 1/600 | 29 |
| 1/1000 | 20 |

The spleens of mice 1 and 4 are used for the fusion.

2.2—Cellular Fusion

Mouse splenocytes are fused with SP2/0-Ag-14 mouse myeloma cells in a ratio of 2/1 in the presence of polyethylene glycol 1500 at 45%. The selection of the hybridomas is carried out by adding hypoxanthine and azaserine to the culture medium 24 and 48 hours after fusion.

The hybridomas are cloned and subcloned by the method of dilution limits.

2.2.1—Results of Screening of the Hybrids and Clones

| HYBRIDS | |
|---|---|
| MOUSE 4 (SPA fusion) | MOUSE 1 (SPB fusion) |
| 2 positive Hybrids in 45 | 6 positive Hybrids in 52 |
| SPA2: 38% prec. | SPB3: 17% prec. |
| SPA19: 7% prec. | SPB5: 67% prec. |
| | SPB8: 53% prec. |
| | SPB13: 68% prec. |
| | SPB25: 13% prec. |
| | SPB34: 17% prec. |

| CLONES | |
|---|---|
| FUSION SPA | FUSION SPB |
| 2 clones retained in 36 | 7 clones retained in 46 |
| SPA2-2: 85% prec. | SPB3-2: 19% prec. |
| SPA19-7: 8% prec. | SPB5-1: 76% prec. |
| | SPB5-2: 71% prec. |
| | SPB5-3: 45% prec. |
| | SPB5-4: 24% prec. |
| | SPB13-1: 79% prec. |
| | SPB13-2: 53% prec. |

| SUBCLONES | |
|---|---|
| SPA FUSION | SPB FUSION |
| 3 subclones retained in 48 | 5 subclones retained in 72 |
| SPA2-2-3: 60% prec. | SPB3-2-19: 21% prec. |
| SPA2-2-22: 33% prec. | SPB5-2-10: 86% prec. |
| SPA2-2-25: 92% prec. | SPB5-4-2: 46% prec. |
| | SPB13-1-7: 87% prec. |
| | SPB13-2-2: 93% prec. |

2.2.2—Production of Anti-SPS Monoclonal Antibodies

The hybridomas are injected by intraperitoneal route to BALB/c female mice treated beforehand with pristane. The monoclonal antibodies are partially purified from ascitic liquids thus produced by precipitation with 18% sodium sulphate. The precipitated proteins are dissolved then dialyzed against the PBS (F18).

2.2.3—Characterization of Anti-SPS Monoclonal Antibodies a) type

The type is determined using an ELISA test. Antibodies of rabbit anti-IgG and mouse anti-IgM (ZYMED) are fixed at the bottom of wells on 96-well plates. After one night at ambient temperature the non-occupied sites are saturated with a solution of bovine serum albumin at 3% in PBS. After one hour of incubation at 37° C. and several washings, the different F18's are deposited in the wells. After incubation and several washings, the goat or rabbit antibodies, anti-class and anti-subclass of mouse immunoglobulins, coupled with peroxidase, are added. After one hour at 37° C., the antibodies are revealed using the $H_2O_2$/ABTS system.

All the anti-SPS monoclonal antibodies are of Ig $G_1$ type.

b) Inhibition of the SPS activity

Determination of the capacity of the antibodies to inhibit the SPS activity is carried out using the technique mentioned above (cf 2.1.1 a) using the F18's.

| Antibodies | Concentration of antibodies (micrograms/ml) | % Inhibition |
|---|---|---|
| SPA2-2-3 | 50 | 0 |
| SPA2-2-22 | 50 | 0 |
| SPA2-2-25 | 50 | 0 |
| SPB3-2-19 | 50 | 0 |
| SPB5-2-10 | 50 | 0 |
| SPB5-4-2 | 50 | 0 |
| SPB13-1-7 | 50 | 50 |
| | 25 | 55 |
| | 5 | 25 |
| | 2.5 | 10 |
| | 1 | 2.1 |
| SPB13-2-2 | 50 | 60.1 |
| | 25 | 59.1 |
| | 5 | 33.8 |
| | 2.5 | 14.2 |
| | 1 | 8.7 | c) Immuno-precipitation of the SPS activity

Determination of the capacity of the antibodies to immuno-precipitate the SPS activity is carried out using the technique mentioned above (cf 2.1.1 b) using the F18's.

| Antibodies | Concentration of antibodies (micrograms/ml) | % Precipitation |
|---|---|---|
| SPA2-2-3 | 50 | 95 |
| | 25 | 92 |
| | 5 | 80 |
| | 2.5 | 40 |
| | 1 | 20 |
| SPA2-2-22 | 50 | 95.7 |
| | 25 | 95 |
| | 10 | 51 |
| | 5 | 48.2 |
| | 2.5 | 25 |
| | 1 | 10 |
| Antibody | | |
| SPA2-2-25 | 50 | 91.3 |
| | 25 | 95.3 |
| | 5 | 90.4 |
| | 2.5 | 22.8 |
| | 1 | 12.5 |
| SPB3-2-19 | 50 | 95 |
| | 25 | 95 |
| | 5 | 27.8 |
| | 2.5 | 17.8 |
| | 1 | 9.3 |

-continued

| | Concentration of antibodies (micrograms/ml) | % Precipitation |
|---|---|---|
| SPB5-2-10 | 50 | 95 |
| | 25 | 95 |
| | 5 | 81.1 |
| | 2.5 | 41.4 |
| | 1 | 22.6 |
| SPB5-4-2 | 50 | 95 |
| | 25 | 95 |
| | 5 | 86.1 |
| | 2.5 | 57.2 |
| | 1 | 26.1 |
| SPB13-1-7 | 50 | 95 |
| | 25 | 95 |
| | 10 | 65.4 |
| | 5 | 48.1 |
| | 2.5 | 15 |
| | 1 | 10 |
| SPB13-2-2 | 50 | 95 |
| | 25 | 95 |
| | 5 | 71.8 |
| | 2.5 | 43.5 |

3—USE OF MONOCLONAL ANTIBODIES FOR THE CHARACTERISATION AND PURIFICATION OF SACCHAROSE PHOSPHATE SYNTHETASE 3.1—Characterization of Maize Saccharose Phosphate Synthetase This characterization is carried out using SPB3-2-19 and SPB13-2-2 antibodies by the technique of immunodetection after transfer of the proteins from an electrophoresis gel under denaturing conditions (SDS PAGE) on to a nitro-cellulose membrane.

After migration in acrylamide gel at 12.5% (Nature 227 (1970) 680–685), the proteins are transferred onto a 0.22 μm nitro-cellulose gel (Schleicher and Schuell) by means of a transfer vat for 30 mn, the initial current being 1 Ampere. The buffer used is the standard electrophoresis buffer (TRIS base 3.03 g/l, Glycine 14.4 g/l, SDS 0.1% pH 8.3) to which 20 % methanol is added.

After transfer, the membrane is put in a saturation bath (Casein 0.5% in PBS) in order to saturate the sites non-occupied with proteins originating from the gel.

After 1 h at 37° C. under gentle agitation, the membrane is washed 3 to 4 times with a washing buffer (Casein 0.1%, Tween 20 0.5%, in PBS) then incubated with a solution of 10 micrograms/ml of the monoclonal antibodies to be tested. A part of the membrane is incubated in parallel with a non-immune antibody (negative control). After incubation for 1 hour at ambient temperature followed by 9 to 10 washings, the membrane is incubated in the presence of a mouse anti-antibody antibody labelled with Iodine 125 diluted in washing buffer (50000 cpm per $cm^2$ of membrane). After incubation for 1 hour at ambient temperature followed by 9 to 10 washings, the membrane is dried then autoradiographed (film X-OMAT AR KODAK and filter amplifier Cronex XTRA Life DUPONT).

Figure 2:
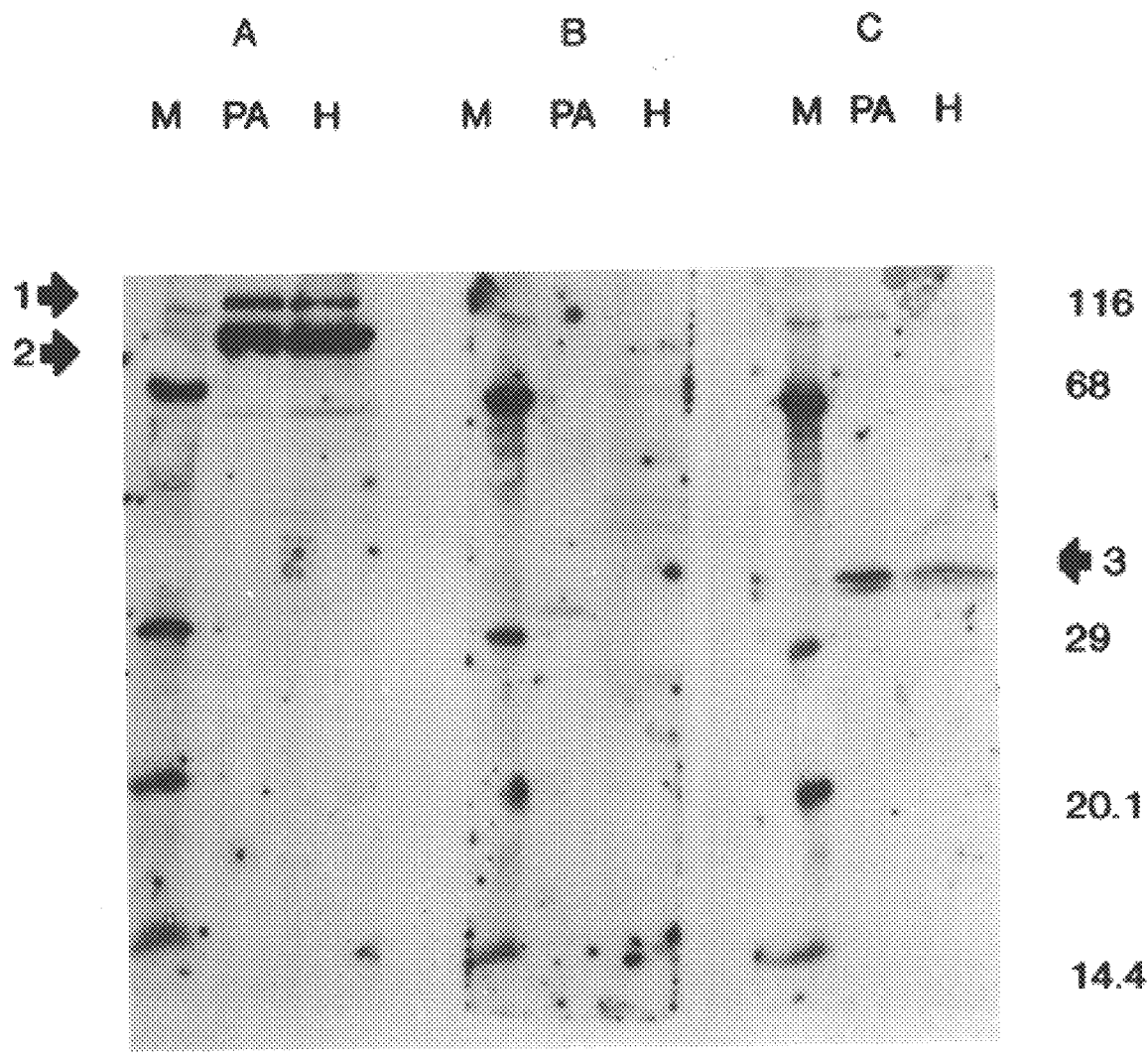
FIG. 2 is an autoradiograph of maize saccharose phosphate synthetase.

An autoradiograph is shown in FIG. 2. A strong signal is observed at the level of the protein bands 120 Kd, 95 Kd and 35 Kd which correlates with the previous results (see first section).

Key to FIG. 2

A: membrane incubated in the presence of the SPB3-2-19 antibody

B: membrane incubated in the presence of an antibody not directed against the SPS (anti-neomycin monoclonal antibody negative Control)

C: membrane incubated in the presence of the SPB13-2-2 antibody M: molecular weight markers radiolabelled with I125 (NEX-188 NEN) B-Galactosidase (116 Kd), Bovine albumin (68 Kd), carbonic anhydrase (29 Kd), Trypsic inhibitor (20.1 Kd), Alpha-Lactalbumin (14.4 Kd), 150000 cpm per deposit PA: deposit of proteins obtained after immunoaffinity chromatography (see below) with the monoclonal antibody SPB13-2-2, approximately 40 micrograms of proteins per deposit.

H: deposit of Heparin fraction, approximately 40 micrograms of proteins per deposit.

3.2—Purification of the Saccharose Phosphate Synthetase by Immunoaffinity

A methodology for purification of the maize Saccharose Phosphate Synthetase on an immunoaffinity support was developed in order to increase the quantity of protein recovered by reducing the number of purification stages and to thus allow sequencing studies.

3.2.1—Preparation of the Immuno-Adsorbant

The F18 (see 2.2.2) corresponding to the SPB13-1-7 antibody or to the SPB13-2-2 antibody is added to activated CH-Sepharose, at the rate of 1 mg of antibody per ml of gel. After incubation for 2 h at ambient temperature, the sites not occupied by antibodies are saturated with 1M ethanolamine pH 9. The support is then washed alternately with an acetate buffer 0.1 M NaCl 0.5 M pH 4 and a TRIS buffer 0.1 M NaCl 0.5 M pH 8. The immunoaffinity support thus prepared is preserved at 4° C. in HEPES buffer 50 mM, $MgCl_2$ 10 mM, EDTA 1 mM, PMSF 1 mM, Sodium nitride (azide) 0.01% pH 7.5.

3.2.2—Immunoaffinity Chromatography

The Heparin fraction corresponding to the purification of the SPS has 50% PEG added to it (see 1.2.1) until a final concentration of 20% PEG is reached. After incubation for 30 mn at 4° C. with slow agitation, the mixture is centrifuged at 1600 g for 30 mn. The protein pellet is taken up in half the volume of starting buffer 50 mM HEPES, 10 mM $MgCl_2$, 1 mM EDTA, 10% ethylene glycol pH 7.5. This stage allows the elimination of the previous buffer which is incompatible with immunoaffinity chromatography and concentration of the proteins. The yield of SPS activity is 80 to 90%.

The solution obtained is applied at a flow rate of 0.1 ml/mn on to 1 ml of immunoaffinity support packed into a column and on which has been fixed an antibody not directed against the SPS (activated CNBr-SEPHAROSE, on which is fixed an anti-neomycin antibody). This first stage allows some contaminants which fix themselves in an aspecific manner on the chromatography support to be eliminated. The non-specific column effluent is in its turn applied on the anti-SPS immunoaffinity support (2 ml in a 11×20 mm column) with a flow rate of 0.1 ml/mn. These two stages are carried out at laboratory temperature. After washing the column with 10 ml of loading buffer then with a washing buffer (loading buffer with NaCl 0.25 M and Tween 20 0.3% added to it) until the absorption in the ultraviolet at 280 nm is close to the base level, the proteins adsorbed on the support are eluted with a solution of triethylamine 50 mM pH 11. This elution is carried out at 4° C. and the immunoaffinity column is turned upside down to obtain an optimum yield. The SDS PAGE profile of the final preparation obtained corresponds to what is obtained with a standard protocol (see 1). It should be noted that the elution method for proteins adsorbed on the immunoaffinity support is non-reversibly inhibitory to the SPS activity but the recovery yield of SPS-linked proteins is optimal by comparison with tests carried out in conditions of native elution. The immunoaffinity column eluant is desalted using the G25 column, against a buffer of 0.14% Glycerol, 0.07% B-mercaptoethanol, 0.04% SDS, 0.9 mM TRIS pH 6.8 (electrophoresis buffer in reducing conditions diluted 70 times). After desalting, the protein preparation is concentrated 70 times using a vacuum concentrator and the SPS proteins are purified by SDS-PAGE (see below).

EXAMPLE 1

Construction of a Complete cDNA Coding for the SPS

A) Sequence of the SPS Polyeptides

Samples of a purified protein preparation obtained as described previously are subjected to an electrophoresis in SDS acrylamide gel.

After electrophoresis, the bands of proteins are detected by treatment: with potassium chloride as described by Bergman and Joernvall (Eur. Jour. Biochem. (1978) 169, 9–12) and the bands observed corresponding to molecular weights of 90 kD and 30 kD are excised. The proteins are electro-eluted from these gel fragments using an Electrophoretic Concentrator according to the manufacturer's recommendations (ISCO; Lincoln, Nebr.) in 4 mM of sodium acetate, pH 8. After electro-elution, the quantities of proteins recovered are determined by comparison with a solution of known concentration of bovine serum albumin (BSA) by staining with Coomassie Blue. Approximately 30 micrograms of 30 kD proteins and 75 micrograms of 90 kD proteins are obtained.

The proteins are concentrated by acetonic precipitation and put in suspension in a buffer of 50 mM of ammonium carbonate, pH 8. Tryptic digestion and HPLC purification are carried out as described by Sturm and Chrispeels (Jour. Biol. Chem. (1987) 262, 13392–13403). Briefly, the digestion is carried out by the addition-of trypsin, and incubation for two hours at 37° C. The digestion is then repeated. The proteins are concentrated by lyophilization and suspended in a buffer of 50 mM of sodium phosphate, pH 2.2. This mixture is subjected to reversed phase HPLC chromatography by application on a C18 column. Elution is carried out using an increasing gradient of acetonitrile. The elution carried out with the buffer mixture of phosphate/acetonitrile gradient is monitored spectrophotometrically at 214 nm. The fractions corresponding to the absorption peaks at 214 nm are collected, lyophilized, suspended in 0.1% trifluoroacetic acid, applied again to the C18 column, and eluted using an acetonitrile gradient The elution carried out with the trifluoroacetic acid/acetontrile gradient is monitored spectrophotometrically at 214 nm. The fractions corresponding to absorption peaks at 214 nm are collected, lyophilized, and subjected to a protein degradation of Edman type using an automatic protein sequencer (Applied Bio-systems; Foster City, Calif.). Sequences of 5 peptides are obtained. (See FIG. 3).

B) Isolation of RNA from Maize Leaves

Whole and fully developed leaves are picked from hybrid 3184 vegetative plants of Pioneer maize of two feet in height (60.96 cm). The leaves are picked late in the morning, deep-frozen in a bath of liquid nitrogen, and kept at −70° C. The total RNA is isolated according to the method of Turpen and Griffith (Biotechniques (1986) 4, 11–15). Briefly, 250 g of material is homogenized in 4 M of guanidine thiocyanate and 2% sarcosyl. The mixture is then centrifuged and the supernatant called clear Lysat is deposited on a bed of 5.7 M CsCl and centrifuged for 5.5 hours at 50,000 rpm. The RNA pellet is dissolved in water, extracted with phenol and chloroform, and precipitated with ethanol. The resultant pellet is suspended in water. The final yield of the isolation of RNA is quantified by UV spectrophotometry. A saturated suspension of cellulose powder/water is added to the RNA/water mixture, at 10% of the total volume, to remove the residual polysaccharides. After centrifuging, the supernatant containing the RNA is applied to a column of oligo (dT)-cellulose as described in Maniatis et al. (Molecular Cloning, A Laboratory Manual, (1982) Cold Spring Harbor, N.Y.). The fraction containing the poly (A) RNA is then applied again to the column. The eluted fraction containing the poly (A) RNA is extracted with phenol and the RNA is precipitated with ethanol.

C) Construction and Screening of a cDNA Library

The synthesis of cDNA is carried out according to the recommendations of the manufacturer (Systeme de Synthese RiboClone™ cDNA by Promega, Madison, Wis.), using five micrograms of poly (A) RNA as matrix, the M-MLV reverse transcriptase (BRL; Bethesda, Md.) is substituted for AMV reverse transcriptase. The EcoRI adapter oligo-nucleotides are added to the cDNA with free ends and the resultant fragments are cloned in an expression vector (LambdaZAP, Stratagene; La Jolla, Calif.) according to the manufacturer's recommendations. The library obtained contains approximately $1.5 \times 10^6$ transformants.

Figure 4:
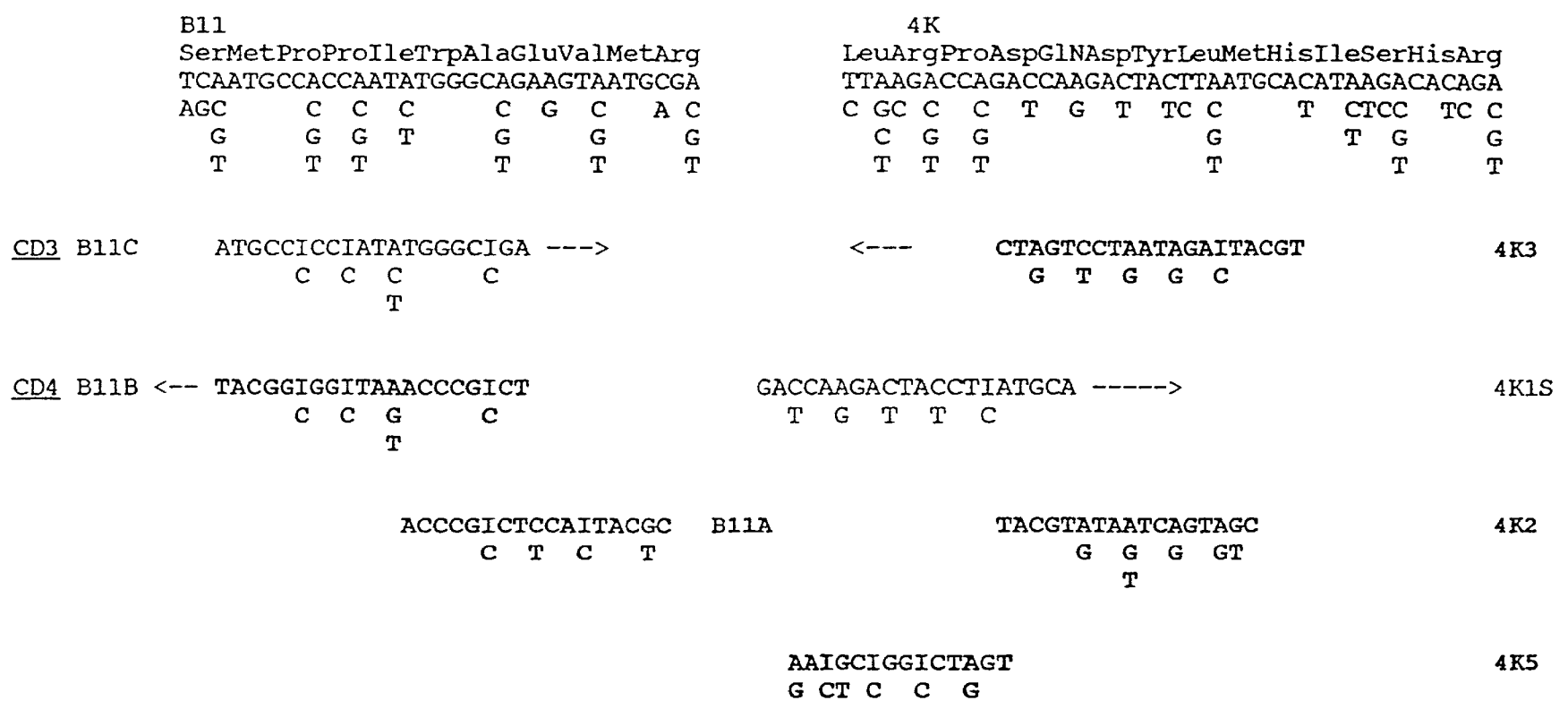
Figure 5A:
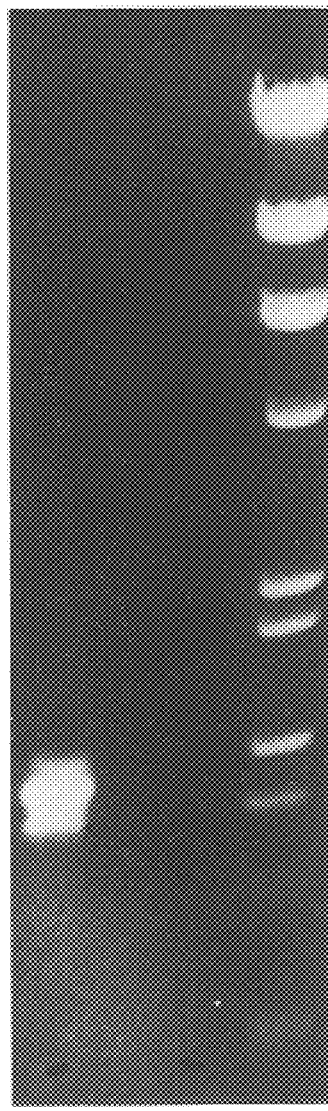
FIG. 5A shows electrophoresis of the CD3 and CD4 PCR.
Figure 5B:
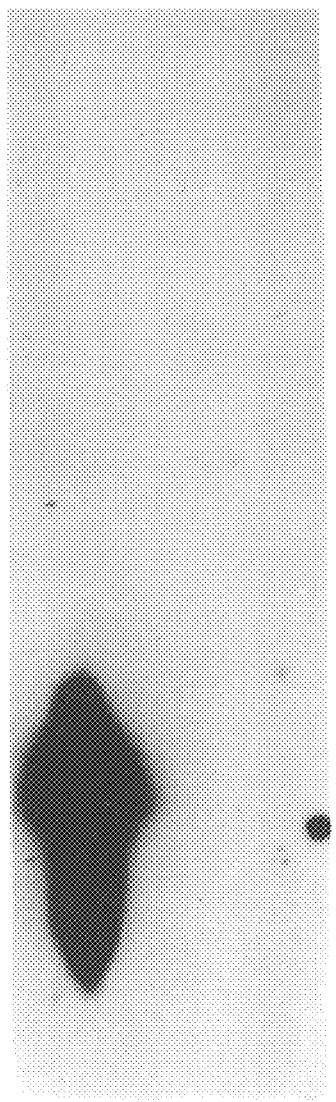
FIG. 5B shows an autoradiograph of the Southern blot of the CD3 and CD4 reactions.

By using the information given by the sequence of peptides of Stage A and the polymerase chain reaction (PCR), a fragment of 1200 bp corresponding to the cDNA of the SPS is generated. The total cDNA obtained from maize leaf RNA is used as a matrix and the degenerated oligonucleotides, synthesized from the data of the sequences of 30 kD and 90 kD protein peptides, are used as initiator. These initiator series are called CD3 and CD4. (FIG. 4). The use of the correct series of initiators, which is CD3, results in a fragment created by PCR reaction. The PCR reaction using the other series of initiators, CD4, does not result in the synthesis of a fragment. FIG. 5. The PCR reaction is carried out according to the manufacturer's recommendations (GeneAmp™ DNA Amplification Reagent Kit and DNA Thermal Cycler of Perkin Elmer Cetus; Norwalk, Conn.) except for the reaction which is continued for 30 cycles, and the rehybridization stages which are carried out at 50° C. for one minute. Southern analysis confirms that the PCR band is not an artefact, as shown in FIG. 5. The 4K5 probe is used because the sequence corresponding to this probe is supposed to be in the 1200 bp fragment if this fragment corresponds to the SPS sequence. The probe hybridizes at the 1200 bp band generated by PCR using the CD3 initiator series but not with the PCR products generated using the CD4 initiator series. (FIG. 5).

Figure 6:
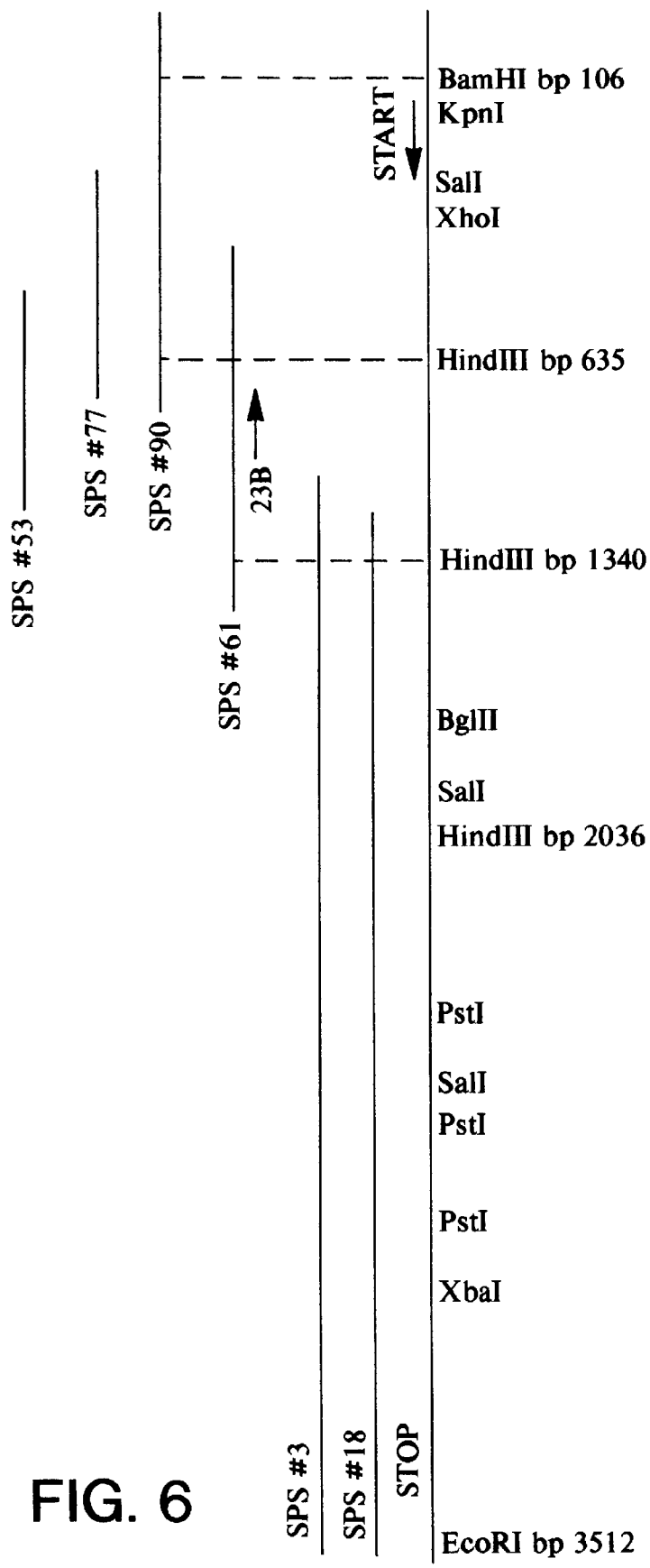
FIG. 6 shows a restriction map of the SPS cDNA.

The 1200 bp fragment generated by PCR is labelled with $^{32}$P [$^{32}$P=radioactive phosphorus] (following the Random Primed DNA Labelling Kit, Boehringer Mannheim, Indianapolis, Ind.) and used as a probe to screen approximately 250,000 plates of a cDNA library. Insertions of positive clones are analyzed by restriction analysis with EcoRI, and the clones possessing the longest insertions SPS#3 and SPS#18, are chosen for a more thorough analysis. (FIG. 6). A HindIII/EcoRI 400 bp fragment of the 5' terminal part of the SPS 3 is isolated, then labelled with $^{32}$P by random labelling (Random Primed DNA Labelling Kit) and used as a probe to rescreen the library. A new clone, called SPS#61, which extends much further upstream than the SPS#3, is isolated. (FIG. 6).

To isolate the cDNA clones which contain more 5' region than the SPS#3 or the SPS#61, a new cDNA library is prepared (following the RiboClone™ cDNA Synthesis System by Promega; Madison, Wis.) using M-MLV reverse transcriptase instead of AMV reverse transcriptase. However, instead of using the oligo (dT) as initiator, a synthetic initiator, 23B, synthesized from the 5' region of the SPS#61 clone, is used. This results in the obtaining of cDNA which contains only the regions upstream of the 5' region of the SPS#61. The library is screened using the EcoRI fragment of SPS#61 labelled with $^{32}$P as a probe, and 16 plates are positive with hybridization. The clones with the longest insertions, SPS#77 and SPS#90, are chosen for a more thorough analysis. The study of the DNA sequence of SPS#77 and SPS#90 shows that the overlapping region (of a size greater than 100 bp) with SPS#61 is identical, and that both extend further upstream in region 5'. (FIG. 6).

The PCR carried out using a single strand cDNA (obtained by reverse transcriptase reaction on the mRNA using an oligo (dT) to bring about the necessary bicatenary initiation for reverse transcriptase) as a matrix and initiators chosen from the SPS#90 and SPS#3 sequences, confirm that SPS#90 and SPS#3 come from the transcription of the same mRNA. The fragment resulting from this PCR reaction is 750 bp in length, compatible with the size expected from study of the DNA sequence. This fragment of 750 bp is sub-cloned in a vector derived from Bluescript in the form of a SALI/HinIII fragment. Four of the resultant sub-clones were partially sequenced and the sequence obtained is identical to the sequence of the previously determined DNA.

D) Assembly of the Sequence Coding for the SPS

The two strands of #90, #61, and #3 are sequenced by the method of Sanger and al. (PNAS (1977) 74; 5463–5467). The reading phase of the SPS determined by knowledge of the peptide sequences, shows that the first methionine codons are placed in positions 112 bp and 250 bp. FIG. 7. The codon in position 112 bp corresponds to a eukaryotic consensus sequence for commencement of translation (Kozak, *Cell* (1986) 44: 283–292) and is placed 54 bp downstream of a TAG stop codon (58 bp). A translational stop is found in the SPS#3 clone, in position 1603 bp. However, another cDNA clone, obtained during the initial screening of the cDNA library (see Example 2), called SPS#18, does not have a stop codon in position 1603. Due to this fact the 1603 bp region of SPS#18 is used to bring about the final construction of complete length (see below).

The complete sequence coding for the SPS can be prepared by combining the 529 bp fragment BamHI/HindIII of the SPS#90, the 705 bp fragment HindIII of the SPS#61, the 686 bp fragment HindIII of the SPS#18, and the 1476 bp fragment HindIII/EcoRI of the SPS#3.

The five peptide sequences derived from SPS 30 kD- and SPS 90 kD- (see Stage A) are found in the protein sequence deduced from study of the open reading phase of the cDNA. (FIG. 7).

EXAMPLE 2

Detection of SPS Polypeptides by Specific Antisera

Figure 8:
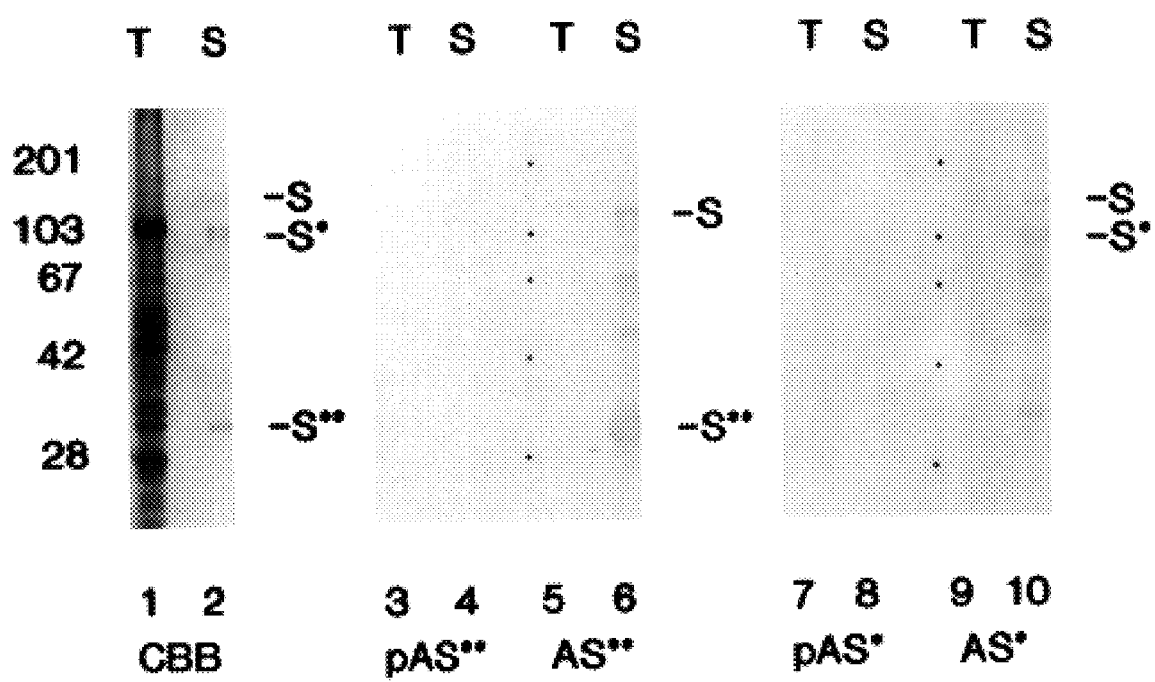
FIG. 8 shows Western characterization of antisera to SPS.

Samples of purified protein preparations obtained by the method described previously are subjected to electrophoresis in SDS acrylamide gel. The proteins of the acrylamide gel are fixed and revealed by staining. The bands corresponding to the 90 kD and 30 kD polypeptides are excised, ground up and injected into rabbits. Western analysis (as described by Oberfelder, *Focus* (1989) 11 (1): 1–5) shows that the antibodies isolated from the serum of the rabbit injected with the SPS 30 peptide recognize the bands corresponding to the SPS 30 and SPS 120 peptides in the SDS acrylamide gel. The antibodies isolated from the serum of the rabbit injected with the SPS 90 peptide recognize the bands corresponding to the SPS 90 and SPS 120 polypeptides. (FIG. 8).

Immunological Localization of SPS in the Maize Plant

Figure 9A:
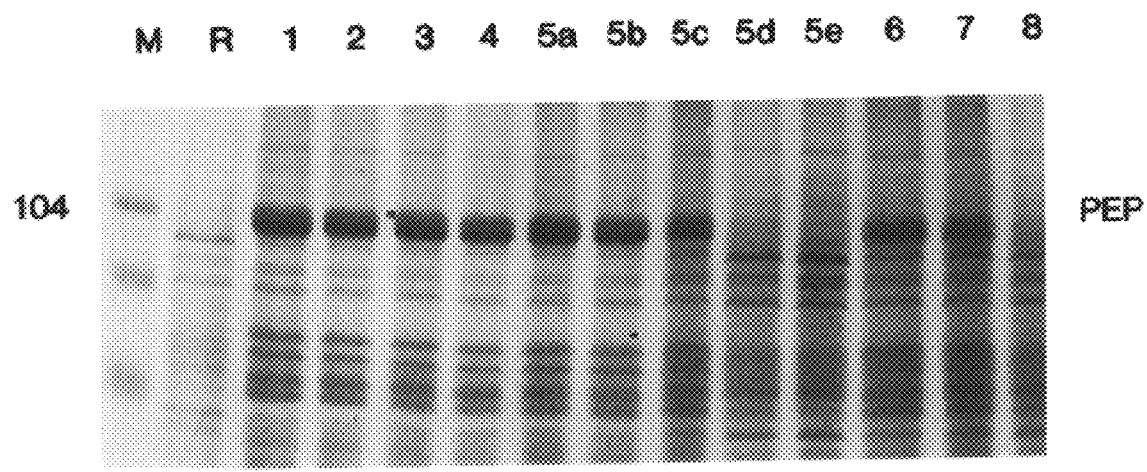
FIG. 9A shows a gel of total proteins isolated from a 30-day old maize plant.
Figure 9B:
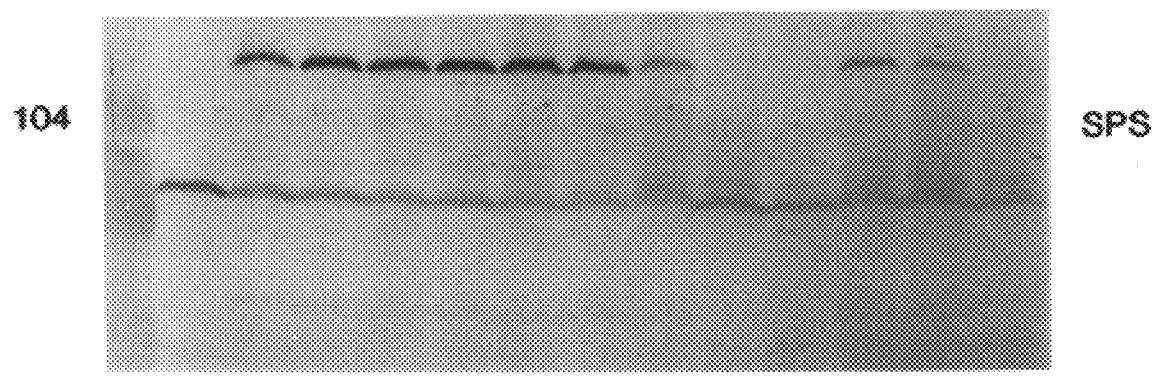
FIG. 9B shows a Western analysis using antisera to SPS directed against the total proteins isolated from a 30-day old maize plant.

The total proteins are extracted from leaves of a 30-day old maize plant, picked at 11 o'clock in the morning, and they are taken to boiling point in an SDS buffer. The protein extracts are deposited on SDS acrylamide gels, in two stages. One gel is stained with Coomassie Blue, while the other is subjected to Western analysis, using a mixture of anti SPS30 and anti SPS90 antisera as a probe. (FIG. 9). The most dense bands appearing on the gel stained with Coomassie Blue are identified as being phosphoenolpyruvate carboxylase (PEPCASE), an enzyme involved in photosynthesis. The Western blot reveals the presence of the SPS. The appearance profile of SPS proteins is very similar to the appearance profile of PEPcase proteins; not present in the roots, and not present in leaf section closest to the stem, nor in the very young leaves. This profile corresponds to the expression of proteins associated with photosynthesis, and is the expected graphical representation for the SPS.

EXAMPLE 3

Construction of Expression Vectors

Construction of a Reading System of Complete Length SPS

An SPS#90 clone (FIG. 6), is digested with HindIII and linked to the 705 bp HindIII fragment of the SPS#61 clone to create a plasmid containing the terminal 5' region of the coding part for the SPS. The resultant plasmid is digested with BamHI and partially digested with HindIII, resulting in a 1340 bp fragment of BamHI/HindIII containing the terminal 5' region of the SPS. The terminal 3' region of the coding part for the SPS is obtained by replacing the 686 bp HindIII fragment (positions 1340–2036) of the SPS#3 clone with the 646 bp HindIII fragment of the SPS#18 (to remove the stop codon). All of the terminal 3' region is then recovered by EcoRI digestion and partial HindIII digestion, resulting in a 1172 bp HindIII/EcoRI fragment. This HindIII/EcoRI fragment, carrying the terminal 3' region, is linked to the BamHI/EcoRI fragment carrying the terminal 5' region in a vector derived from pUC digested by BamHi/EcoRI, to create a carrying all of the region coding for the SPS, that being 3406 bp.

Construction of the Small Sub-Unit Promoter Cassette of Ribulose-1,5-bisphosphate Carboxylase of Tobacco [*21]

The region coding for the SPS can be cloned in a convenient manner in the form of a BamHI/EcoRI fragment (106 pb–3506 bp) in a small sub-unit promoter cassette of tobacco (SSU).

An SSU promoter cassette, for the expression of the SPS, can be prepared as follows. The SSU promoter region comes from the PCGN627 (described below) in the form of an Asp718/SalI fragment, and linked to a plasmid pCGN1431 digested by Asp718/SalI (described below), resulting in a cassette containing the SSU promoter and the tml 3' region separated by a DNA fragment carrying the restriction sites.

After ligation of the DNA fragment coding for the SPS in the SSU/tml3' promoter cassette, the SSU/SPS/tml3' region can be linked in a binary vector and integrated in a plant genome by transformation via Agrobacterium tumefaciens.

[*3] pCGN627

The 3.4 kb EcoRI fragment of the TSSU3-8 (O'Neal et al., *Nucleic Acids Res* (1987) 15; 8661–8677), containing the promoter region of the small sub-unit of ribulose 1,5-bisphosphate carboxylase, is cloned in the EcoRI site of the M13mp18 (Yanisch-Perron et al., *Gene* (1985) 53: 103–119) to produce a M13 8B clone. The single strand DNA of this M13 8B phage is used as a matrix to prolong the initiation of oligonucleotide "Probe 1" whose structure is defined in O'Neal's article (O'Neal et al., *Nucleic Acids Research* (1987) 15; 8661–8677) by using the Klenow fragment of the DNA polymerase I. The products of this reaction with polymerase are treated with mung bean nuclease (Mung Bean Nuclease) and then digested with HindIII to produce a 1450 bp fragment containing the SSU promoter region. This fragment is cloned in pUC18 digested by HindIII-SmaI (Yanisch-Perron et al., *Gene* (1985) 53: 103–119) to produce pCGN625.

pCGN625 is digested by the restriction enzyme HindIII, the terminal regions are filled with the Klenow fragment of the DNA polymerase I and the plasmid thus obtained is redigested with the restriction enzyme EcoRI. The filled EcoRI/HindIII fragment containing the SSU promoter region is linked by ligation to the plasmid pUC18 digested by SmaI/EcoRI to produce pCGN627.

pCGN1431 contains the double promoter CAMV 35S and the tml 3' region with a multiple cloning site between them. This promoter/terminator cassette is contained in a vector derived from pUC which contains a chloramphenicol resistance gene instead of the ampicillin resistance gene. The cassette is flanked with multiple restriction sites for easy use.

A) Construction of pCGN986 pCGN986 contains the 35S promoter of the cauliflower mosaic virus (CaMV35) and a tml-3' region of the T-DNA with multiple restriction sites between them. The plasmid pCGN986 is derived from another cassette, pCGN206, containing the promoter of CaMV35S and a different 3' region, the VI terminal 3' region of the CaMV region. The promoter of CaMV35S is cloned in the form of an AluI fragment (7144–7734 bp) (Gardner et al., *Nucl. Acids Res.* (1981) 9: 2871–2888) in a HincII site of M13mp7 (Messing et al., *Nucl. Acids Res* (1981) 9: 309–321) to create C614. The digestion by the restriction enzyme EcoRI of C614 produces the EcoRI fragment containing the 35S promoter which is cloned in a restriction site of pUC8 (Vieira and Messing, *Gene* (1982) 19: 259–268) to produce pCGN147.

pCGN148a containing a promoter region, a label allowing a selection (Kanamycin with 2 ATG'S), and a 3' region, is prepared by digestion of the plasmid pCGN528 with BglII and insertion of the promoter fragment BamHi-BhlII of the pCGN147. This fragment is cloned in the BglII site of the pCGN528 seeing to it that the the BglII site is close to the Kanamycin gene of the pCGN528.

The shuttle vector used for this construction of pCGN528 is achieved as follows: pCGN535 is obtained by digestion of a plasmid containing Tn5, (which carries a Kanamycin resistance gene) (Jorgensen et al., *Mol. Gen. Genet.* (1979) 177: 65), with HindIII-BamHI and by insertion of the HindIII-BamHI fragment containing the Kanamycin resistance gene in the HindIII-BamHI sites of the pACYC184 tetracylcin resistance gene (Chang and Cohen, *J. Bacteriol.* (1978) 134: 1141–1156). pCGN526 is obtained by inserting the BamHI 19 fragment of pTiA6 (Thomashow et al., *Cell* (1980) 19: 729–739) modified with XhoI adapters at the level of the SmaI site, in the BamHI site of pCGN525. pCGN528 is obtained by removing the small Xho fragment followed by a new ligation.

The plasmid pCGN149a is obtained by cloning the BamHI fragment of the pMB9KanXXI carrying the Kanamycin resistance gene in the BamHI site of the pCGN148a. pMB9KanXXI is a vector derived from the pUC4K plasmid (Vieira and Messing, *Gene* (1982) 19: 259–268) which has no XhoI restriction site but which contains the Kanamycin resistance gene of Tn903 allowing an efficient selection in Agrobacterium. [*4]

pCGN149a is digested with HindIII and BamHI and linked with pUC8 (Vieira and Messing, supra) digested with HindIII and BamHI to produce pCGN169. This eliminates the Kanamycin label of Tn903. pCGN565 and pCGN169 are both digested with HindIII and PstI and religated to form pCGN203, a plasmid containing the CaMV 35S promoter and a part of the terminal 5' region of the Kanamycin Tn5 gene (up to site PstI) (Jorgensen et al., *Mol.Gen. Genet.* (1979) 177: 65). A 3' regulatory region is added to the pCGN203 from the pCGN204 plasmid (a EcoRI fragment of CaMV (408–6105 bp) containing the VI terminal 3' region cloned in pUC18 (Gardner et al., *Nucl.Acids Res.* (1981) 9: 2871–2888) by digestion with HindIII and PstI and ligation. The resultant cassette, pCGN206, is the base plasmid for the construction of the pCGN986.

The tml 3' sequences of pTiA6 T-DNA are sub-cloned from the BamHI19 fragment of the T-DNA (Thomashow et al., *Cell* (1980) 19: 729–739) in the form of a BamHI-EcoRI fragment (nucleotides 9062 to 12823, following the numbering of Barker (Barker et al., *Plant Mo. Biol.* (1983) 2: 335–350). This sequence is combined with the pACYC184 replication origin (EcoRI-HindII fragment) (Chang and Cohen, *J.Bacteriol.* (1978) 134: 1141–1156) and a marker of gentamycin resistance of the pLB41 plasmid, (BamHI-HindII fragment) (D. Figurski) to produce pCGN417.

The single SmaI site of pCGN417 (nucleotide 11207 of the BamHI19 fragment) is changed into an SacI site by using adapters and the BamHI-SacI fragment is sub-cloned in pCGN565 to give pCGN971. The BamHI site of pCGN971 is changed into an EcoRI site by using adapters to produce pCGN971E. The EcoRI-SacI fragment of the pCGN971E plasmid, containing the tml 3' regulatory region, is joined to the pCGN206 plasmid after digestion by EcoRI and SacI to give pCGN975. The small part of the Tn5 Kanamycin resistance gene is removed from the terminal 3' region of the CaMV 35S promoter by digestion with SalI and BglII, by making the ends free and adding SalI adapters. The final expression cassette pCGN986 contains the CaMV 35s promoter followed by two SalI sites, an XbaI, BamHI, SmaI, KpnI site and the tml 3' region (nucleotides 11207–9023 of the T-DNA).

B) Construction of pCGN164

The ALuI fragment of the CaMV (7144–7735 bp) (Gardner et al., *Nucl.Acids Res.* (1981) 9: 2871–2888) is obtained by digestion with AluI and cloning in the HincII site of M13mp7 (Vieira and Messing, *Gene* (1982) 19: 259–268) to create C614. Digestion of C614 by the restriction enzyme EcoRI produces the EcoRI fragment containing the 35S promoter. This fragment is cloned in the EcoRI site of pUC8 (Vieira and Messing, supra) to produce pCGN146. In order to decrease slightly the promoter region, the BglII site (7670 bp) is treated with BglII and Bal31 and subsequently a BglII adapter is attached to the DNA treated by Bal31 to produce pCGN147. pCGN147 is digested with EcoRI/HphI and the resultant EcoRI-HphI fragment containing the 35S promoter is transferred into an M13mp8 vector digested by EcoRI and SmaI (Vieira and Messing, supra) to create pCGN164.

C) Construction of pCGN638

The digestion of CaMV10 (Gardner, et al., *Nucl. Acids Res.* (1981) 9: 2871–2888) with BglII produces a BglII fragment containing a 35S promoter region (6493–7670 bp) which is linked to the BamHI site of pUC19 (Norrander et al., *Gene* (1983) 26: 101–106) to create pCGN638.

D) Construction of pCGN2113 pCGN164 is digested with EcoRV and BamHI to free the EcoRV-BamHI fragment containing a part of the 35S promoter (7340–7433 bp). The pCGN638 plasmid is digested with HindIII and EcoRV to free a HindIII-EcoRV fragment containing a different part of the 35S promoter (6493–7340 bp). These two fragments are linked in pCGN986 previously digested with HindIII and BamHI to remove the HindIII-BamHI fragment of the 35S promoter; this ligation produces pCGN639, which contains the skeleton of the plasmid and the tml-3' region of the pCGN986 and the two fragments of the 35S promoter of pCGN164 and pCGN638. pCGN638 is digested with EcoRV and DdeI to free a fragment of the 35S promoter (7070–7340 bp). The fragment is treated with the Klenow fragment of the DNA polymerase I to create free terminal regions and is linked to the EcoRV site of pCGN639 to produce pCGN2113 which has the fragment in a good orientation. The pCGN2113 plasmid was deposited at the ATCC (American Type Culture Collection) on 22nd Mar. 1989, Accession Number 40587.

E) Construction of pCGN1761 pCGN2113 is digested by the EcoRI restriction enzyme and the plasmid is linked in the presence of a synthetic adapter containing an XbaI site and a BamHI site (the adapter contained the cohesive EcoRI terminii of each side, but the adjacent bases are such that an EcoRI site is not reconstructed at this site) to produce pCGN2113M. pCGN2113M is digested completely by SacI and then subjected to a partial digestion by BamHI. This DNA is then treated with the T4 DNA polymerase to create free terminii and an EcoRI adapter is linked in the plasmid to the free terminii. After transformation a clone carrying a plasmid having an EcoRI site between the promoter and the intact tml-3' region is chosen and designated pCGN1761.

F) Construction of pCGN1431

The SalI-EcoRI fragment of pCGN2113, which contains the complete promoter/multiple restriction site—tml 3' cassette is recovered by SalI-EcoRI digestion and cloned in the plasmid pCGN565 digested by SalI-EcoRI to create pCGN2120. The pCGN565 plasmid is a cloning vector based on a pUC8-Cm vector carrying the chloramphenicol resistance gene (K. Buckley, Ph.D.Thesis, UC San Diego 1985), but containing the multi-restriction site of pUC18 (Yanisch-Perron et al., Gene (1985) 53: 103–119). pCGN2120 is digested totally with PstI and then linked again. A clone having eliminated only the PstI-PstI fragment of 858 bp.(9207–10065, Barker et al., 1983 supra) of the tml 3' region is called pCGN1431.

BRIEF DESCRIPTION OF THE DRAWINGS

FIG. 1 is the SDS-PAGE profile illustrating the purification of the maize saccharose phosphate synthetase.

FIG. 2 is an autoradiograph of maize saccharose phosphate synthetase showing strong signals at protein bands 120 kd, 95 kd and 35 kd.

FIG. 3: peptide sequences derived from the SPS protein. All the peptides are oriented N→C terminal.

FIG. 4: structure of the oligonucleotides used for the CD3 and CD4 PCR reactions in connection with the peptides (anti-direction sequences are presented in bold). The arrows indicate the direction towards which the oligonucleotides will initiate the catalysis reaction by polymerase.

FIG. 5 A: electrophoresis using agarose gel of the CD3 and CD4 PCR reactions. Dimensions are given in kb.

FIG. 5 B: shows an autoradiograph of the Southern blot of the CD3 and CD4 reactions read using the 4K5 oligonucleotide probe.

FIG. 6: restriction map of the cDNA coding for the SPS. The upper part represents the restriction map of the total DNA fragment coding for the SPS. The lower parts represent the structure of the different clones having been allowed by combination to achieve this restriction map. The initiation and termination translation codons are indicated.

FIG. 7: sequence of the cDNA coding for the SPS. The sequences of the SPS 90, PSP 61 and SPS 3 clones are fused at the points indicated on FIG. 4. The three reading phases have been translated. Only the open reading phase corresponding to the SPS is indicated under the nucleotide sequence. All the peptide sequences obtained during the purification and sequencing of the SPS (peptides of FIG. 3) are indicated in the sequence.

FIG. 8: characterization by the Western technique of the anti-SPS 90 and anti-SPS 30 rabbit sera. pAS=non-immune serum, rabbit SPS 30; AS=immunized serum, SPS 30; pAS=non-immune serum, rabbit SPS 90; AS*=anti SPS 90 immunized serum.

Molecular weight markers to the left,

S=SPS 120 kd polypeptide; S*=SPS 90 kd polypeptide; S**=SPS 30 kd polypeptide.

FIG. 9 A: gel of total proteins isolated from a 30-day old maize plant, stained with Coomassie Blue.

M=size marker; R=roots; 1–8=number of leaves counting from the base of the plant. Leaf 5 was cut into 5 segments starting from the end of the leaf (5a) up to the end of the sheath (5e). PEP=phosphoenolpyruvate carboxylase.

FIG. 9 B: shows the results of a Western analysis using a mixture of anti-SPS 30 and anti-SPS 90 sera directed against the total proteins isolated from a 30-day old maize plant. The signal corresponding to the SPS appears at the 120–140 kd level.

What is claimed is:

1. A cDNA encoding maize saccharose phosphate synthetase.

2. The cDNA of claim 1 having the nucleotide sequence of Sequence ID No.: 12.

3. A chimeric DNA construct comprised of a coding sequence for maize saccharose phosphate synthetase operably joined to flanking regulatory regions not naturally associated with said coding sequence.

4. A plant transformation vector comprised of the chimeric DNA construct of claim 3.

5. A transgenic plant comprised of the chimeric DNA construct of claim 3.

6. Seeds of the plants of claim 5 wherein said seeds comprise said chimeric DNA construct.

* * * * *

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 4
      (B) TYPE: Amino Acid
      (C) STRANDEDNESS: Single
      (D) TOPOLOGY: Unknown (ii) MOLECULE TYPE: Peptide (xi) SEQUENCE DESCRIPTION:SEQ ID NO: 1:

Thr Trp Ile Lys
1

(2) INFORMATION FOR SEQ ID NO: 2:

(i) SEQUENCE CHARACTERISTICS:
        (A) LENGTH:  7
        (B) TYPE:  Amino Acid
        (C) STRANDEDNESS:  Single
        (D) TOPOLOGY:  Unknown (ii) MOLECULE TYPE:  Peptide (xi) SEQUENCE DESCRIPTION:SEQ ID NO: 2:

Tyr Val Val Glu Leu Ala Arg
1               5

(2) INFORMATION FOR SEQ ID NO: 3:

(i) SEQUENCE CHARACTERISTICS:
        (A) LENGTH:  11
        (B) TYPE:  Amino Acid
        (C) STRANDEDNESS:  Single
        (D) TOPOLOGY:  Unknown (ii) MOLECULE TYPE:  Peptide (xi) SEQUENCE DESCRIPTION:SEQ ID NO: 3:

Ser Met Pro Pro Ile Trp Ala Glu Val Met Arg
1               5                   10

(2) INFORMATION FOR SEQ ID NO: 4:

(i) SEQUENCE CHARACTERISTICS:
        (A) LENGTH:  14
        (B) TYPE:  Amino acid
        (C) STRANDEDNESS:  Single
        (D) TOPOLOGY:  Unknown (ii) MOLECULE TYPE:  Peptide (xi) SEQUENCE DESCRIPTION:SEQ ID NO: 4:

Leu Arg Pro Asp Gln Asp Tyr Leu Met His Ile Ser His Arg
1               5                   10

(2) INFORMATION FOR SEQ ID NO: 5:

(i) SEQUENCE CHARACTERISTICS:
        (A) LENGTH:  7
        (B) TYPE:  Amino acid
        (C) STRANDEDNESS:  Single
        (D) TOPOLOGY:  Unknown (ii) MOLECULE TYPE:  Peptide (xi) SEQUENCE DESCRIPTION:SEQ ID NO: 5:

Trp Ser His Asp Gly Ala Arg
1               5

(2) INFORMATION FOR SEQ ID NO: 6:

(i) SEQUENCE CHARACTERISTICS:
        (A) LENGTH:  12
        (B) TYPE:  Nucleic acid
        (C) STRANDEDNESS:  Unknown
        (D) TOPOLOGY:  Unknown (ii) MOLECULE TYPE:  cDNA (xi) SEQUENCE DESCRIPTION:SEQ ID NO: 6:

```
ACG TGG ATC AAG                                                          12
Thr Trp Ile Lys
1
```

(2) INFORMATION FOR SEQ ID NO: 7:

(i) SEQUENCE CHARACTERISTICS:
        (A) LENGTH: 21
        (B) TYPE: Nucleic acid
        (C) STRANDEDNESS: Unknown
        (D) TOPOLOGY: Unknown (ii) MOLECULE TYPE: cDNA (xi) SEQUENCE DESCRIPTION:SEQ ID NO: 7:

```
TAT GTG GTC GAA CTT GCA AGA                                              21
Tyr Val Val Glu Leu Ala Arg
1               5
```

(2) INFORMATION FOR SEQ ID NO: 8:

(i) SEQUENCE CHARACTERISTICS:
        (A) LENGTH: 33
        (B) TYPE: Nucleic acid
        (C) STRANDEDNESS: Unknown
        (D) TOPOLOGY: Unknown (ii) MOLECULE TYPE: cDNA (xi) SEQUENCE DESCRIPTION:SEQ ID NO: 8:

```
TCA ATG CCC CCA ATT TGG GCC GAA GTG ATG CGG                              33
Ser Met Pro Pro Ile Trp Ala Glu Val Met Arg
1               5                   10
```

(2) INFORMATION FOR SEQ ID NO: 9:

(i) SEQUENCE CHARACTERISTICS:
        (A) LENGTH: 42
        (B) TYPE: Nucleic acid
        (C) STRANDEDNESS: Unknown
        (D) TOPOLOGY: Unknown (ii) MOLECULE TYPE: cDNA (xi) SEQUENCE DESCRIPTION:SEQ ID NO: 9:

```
CTG CGC CCA GAT CAG GAC TAT CTG ATG CAC ATC ACG CAC CGC                  42
Leu Arg Pro Asp Gln Asp Tyr Leu Met His Ile Ser His Arg
1               5                   10
```

(2) INFORMATION FOR SEQ ID NO: 10:

(i) SEQUENCE CHARACTERISTICS:
        (A) LENGTH: 21
        (B) TYPE: Nucleic acid
        (C) STRANDEDNESS: Unknown
        (D) TOPOLOGY: Unknown (ii) MOLECULE TYPE: cDNA (xi) SEQUENCE DESCRIPTION:SEQ ID NO: 10:

```
TGG TCC CAT GAC GGC GCG AGG                                              21
Trp Ser His Asp Gly Ala Arg
1               5
```

(2) INFORMATION FOR SEQ ID NO: 11:

(i) SEQUENCE CHARACTERISTICS:
        (A) LENGTH: 1068

(B) TYPE: Amino acid
(C) STRANDEDNESS: Single
(D) TOPOLOGY: Unknown (ii) MOLECULE TYPE: Peptide (xi) SEQUENCE DESCRIPTION:SEQ ID NO: 11:

```
Met Ala Gly Asn Glu Trp Ile Asn Gly Tyr Leu Glu Ala Ile Leu
 1               5                  10                  15

Asp Ser His Thr Ser Ser Arg Gly Ala Gly Gly Gly Gly Gly Gly
                20                  25                  30

Gly Asp Pro Arg Ser Pro Thr Lys Ala Ala Ser Pro Arg Gly Ala
                35                  40                  45

His Met Asn Phe Asn Pro Ser His Tyr Phe Val Glu Glu Val Val
                50                  55                  60

Lys Gly Val Asp Glu Ser Asp Leu His Arg Thr Trp Ile Lys Val
                65                  70                  75

Val Ala Thr Arg Asn Ala Arg Glu Arg Ser Thr Arg Leu Glu Asn
                80                  85                  90

Met Cys Trp Arg Ile Trp His Leu Ala Arg Lys Lys Lys Gln Leu
                95                  100                 105

Glu Leu Glu Gly Ile Gln Arg Ile Ser Ala Arg Arg Lys Glu Gln
                110                 115                 120

Glu Gln Val Arg Arg Glu Ala Thr Glu Asp Leu Ala Glu Asp Leu
                125                 130                 135

Ser Glu Gly Glu Lys Gly Asp Thr Ile Gly Glu Leu Ala Pro Val
                140                 145                 150

Glu Thr Thr Lys Lys Lys Phe Gln Arg Asn Phe Ser Asp Leu Thr
                155                 160                 165

Val Trp Ser Asp Asp Asn Lys Glu Lys Lys Leu Tyr Ile Val Leu
                170                 175                 180

Ile Ser Val His Gly Leu Val Arg Gly Glu Asn Met Glu Leu Gly
                185                 190                 195

Arg Asp Ser Asp Thr Gly Gly Gln Val Lys Tyr Val Val Glu Leu
                200                 205                 210

Ala Arg Ala Met Ser Met Met Pro Gly Val Tyr Arg Val Asp Leu
                215                 220                 225

Phe Thr Arg Gln Val Ser Ser Pro Asp Val Asp Trp Ser Tyr Gly
                230                 235                 240

Glu Pro Thr Glu Met Leu Cys Ala Gly Ser Asn Asp Gly Glu Gly
                245                 250                 255

Met Gly Glu Ser Gly Gly Ala Tyr Ile Val Arg Ile Pro Cys Gly
                260                 265                 270

Pro Arg Asp Lys Tyr Leu Lys Lys Glu Ala Leu Trp Pro Tyr Leu
                275                 280                 285

Gln Glu Phe Val Asp Gly Ala Leu Ala His Ile Leu Asn Met Ser
                290                 295                 300

Lys Ala Leu Gly Glu Gln Val Gly Asn Gly Arg Pro Val Leu Pro
                305                 310                 315

Tyr Val Ile His Gly His Tyr Ala Asp Ala Gly Asp Val Ala Ala
                320                 325                 330

Leu Leu Ser Gly Ala Leu Asn Val Pro Met Val Leu Thr Gly His
                335                 340                 345

Ser Leu Gly Arg Asn Lys Leu Glu Gln Leu Leu Lys Gln Gly Arg
                350                 355                 360
```

```
Met Ser Lys Glu Glu Ile Asp Ser Thr Tyr Lys Ile Met Arg Arg
            365                 370                 375

Ile Glu Gly Glu Glu Leu Ala Leu Asp Ala Ser Glu Leu Val Ile
            380                 385                 390

Thr Ser Thr Arg Gln Glu Ile Asp Glu Gln Trp Gly Leu Tyr Asp
            395                 400                 405

Gly Phe Asp Val Lys Leu Glu Lys Val Leu Arg Ala Arg Ala Arg
            410                 415                 420

Arg Gly Val Ser Cys His Gly Arg Tyr Met Pro Arg Met Val Val
            425                 430                 435

Ile Pro Pro Gly Met Asp Phe Ser Asn Val Val His Glu Asp
            440                 445                 450

Ile Asp Gly Asp Gly Asp Val Lys Asp Ile Val Gly Leu Glu
            455                 460                 465

Gly Ala Ser Pro Lys Ser Met Pro Pro Ile Trp Ala Glu Val Met
            470                 475                 480

Arg Phe Leu Thr Asn Pro His Lys Pro Met Ile Leu Ala Leu Ser
            485                 490                 495

Arg Pro Asp Pro Lys Lys Asn Ile Thr Thr Leu Val Lys Ala Phe
            500                 505                 510

Gly Glu Cys Arg Pro Leu Arg Glu Leu Ala Asn Leu Thr Leu Ile
            515                 520                 525

Met Gly Asn Arg Asp Asp Ile Asp Asp Met Ser Ala Gly Asn Ala
            530                 535                 540

Ser Val Leu Thr Thr Val Leu Lys Leu Ile Asp Lys Tyr Asp Leu
            545                 550                 555

Tyr Gly Ser Val Ala Phe Pro Lys His His Asn Gln Ala Asp Val
            560                 565                 570

Pro Glu Ile Tyr Arg Leu Ala Ala Lys Met Lys Gly Val Phe Ile
            575                 580                 585

Asn Pro Ala Leu Val Glu Pro Phe Gly Leu Thr Leu Ile Glu Ala
            590                 595                 600

Ala Ala His Gly Leu Pro Ile Val Ala Thr Lys Asn Gly Gly Pro
            605                 610                 615

Val Asp Ile Thr Asn Ala Leu Asn Asn Gly Leu Leu Val Asp Pro
            620                 625                 630

His Asp Gln Asn Ala Ile Ala Asp Ala Leu Leu Lys Leu Val Ala
            635                 640                 645

Asp Lys Asn Leu Trp Gln Glu Cys Arg Arg Asn Gly Leu Arg Asn
            650                 655                 660

Ile His Leu Tyr Ser Trp Pro Glu His Cys Arg Thr Tyr Leu Thr
            665                 670                 675

Arg Val Ala Gly Cys Arg Leu Arg Asn Pro Arg Trp Leu Lys Asp
            680                 685                 690

Thr Pro Ala Asp Ala Gly Ala Asp Glu Glu Phe Leu Glu Asp
            695                 700                 705

Ser Met Asp Ala Gln Asp Leu Ser Leu Arg Leu Ser Ile Asp Gly
            710                 715                 720

Glu Lys Ser Ser Leu Asn Thr Asn Asp Pro Leu Trp Phe Asp Pro
            725                 730                 735

Gln Asp Gln Val Gln Lys Ile Met Asn Asn Ile Lys Gln Ser Ser
            740                 745                 750

Ala Leu Pro Pro Ser Met Ser Ser Val Ala Ala Glu Gly Thr Gly
            755                 760                 765
```

```
Ser Thr Met Asn Lys Tyr Pro Leu Leu Arg Arg Arg Arg Leu
            770                 775                 780

Phe Val Ile Ala Val Asp Cys Tyr Gln Asp Asp Gly Arg Ala Ser
            785                 790                 795

Lys Lys Met Leu Gln Val Ile Gln Glu Val Phe Arg Ala Val Arg
            800                 805                 810

Ser Asp Ser Gln Met Phe Lys Ile Ser Gly Phe Thr Leu Ser Thr
            815                 820                 825

Ala Met Pro Leu Ser Glu Thr Leu Gln Leu Leu Gln Leu Gly Lys
            830                 835                 840

Ile Pro Ala Thr Asp Phe Asp Ala Leu Ile Cys Gly Ser Gly Ser
            845                 850                 855

Glu Val Tyr Tyr Pro Gly Thr Ala Asn Cys Met Asp Ala Glu Gly
            860                 865                 870

Lys Leu Arg Pro Asp Gln Asp Tyr Leu Met His Ile Ser His Arg
            875                 880                 885

Trp Ser His Asp Gly Ala Arg Gln Thr Ile Ala Lys Leu Met Gly
            890                 895                 900

Ala Gln Asp Gly Ser Gly Asp Ala Val Glu Gln Asp Val Ala Ser
            905                 910                 915

Ser Asn Ala His Cys Val Ala Phe Leu Ile Lys Asp Pro Gln Lys
            920                 925                 930

Val Lys Thr Val Asp Glu Met Arg Glu Arg Leu Arg Met Arg Gly
            935                 940                 945

Leu Arg Cys His Ile Met Tyr Cys Arg Asn Ser Thr Arg Leu Gln
            950                 955                 960

Val Val Pro Leu Leu Ala Ser Arg Ser Gln Ala Leu Arg Tyr Leu
            965                 970                 975

Ser Val Arg Trp Gly Val Ser Val Gly Asn Met Tyr Leu Ile Thr
            980                 985                 990

Gly Glu His Gly Asp Thr Asp Leu Glu Glu Met Leu Ser Gly Leu
            995                 1000                1005

His Lys Thr Val Ile Val Arg Gly Val Thr Glu Lys Gly Ser Glu
            1010                1015                1020

Ala Leu Val Arg Ser Pro Gly Ser Tyr Lys Arg Asp Asp Val Val
            1025                1030                1035

Pro Ser Glu Thr Pro Leu Ala Ala Tyr Thr Thr Gly Glu Leu Lys
            1040                1045                1050

Ala Asp Glu Ile Met Arg Ala Leu Lys Gln Val Ser Lys Thr Ser
            1055                1060                1065

Ser Gly Met (2) INFORMATION FOR SEQ ID NO: 12:

(i) SEQUENCE CHARACTERISTICS:
        (A) LENGTH: 3509
        (B) TYPE: Nucleic acid
        (C) STRANDEDNESS: Unknown
        (D) TOPOLOGY: Unknown (ii) MOLECULE TYPE: cDNA (xi) SEQUENCE DESCRIPTION:SEQ ID NO: 12:

GAATTCCGGC GTGGGCGCTG GGCTAGTGCT CCCGCAGCGA GCGATCTGAG          50

AGAACGGTAG AGTTCCGGCC GGGCGCGCGG GAGAGGAGGA GGGTCGGGCG          100
```

-continued

```
GGGAGGATCC G                                                                                    111

ATG GCC GGG AAC GAG TGG ATC AAT GGG TAC CTG GAG GCG ATC CTC                                     156
Met Ala Gly Asn Glu Trp Ile Asn Gly Tyr Leu Glu Ala Ile Leu
 1               5                  10                  15

GAC AGC CAC ACC TCG TCG CGG GGT GCC GGC GGC GGC GGC GGG                                         201
Asp Ser His Thr Ser Ser Arg Gly Ala Gly Gly Gly Gly Gly Gly
                20                  25                  30

GGG GAC CCC AGG TCG CCG ACG AAG GCG GCG AGC CCC CGC GGC GCG                                     246
Gly Asp Pro Arg Ser Pro Thr Lys Ala Ala Ser Pro Arg Gly Ala
                35                  40                  45

CAC ATG AAC TTC AAC CCC TCG CAC TAC TTC GTC GAG GAG GTG GTC                                     291
His Met Asn Phe Asn Pro Ser His Tyr Phe Val Glu Glu Val Val
                50                  55                  60

AAG GGC GTC GAC GAG AGC GAC CTC CAC CGG ACG TGG ATC AAG GTC                                     336
Lys Gly Val Asp Glu Ser Asp Leu His Arg Thr Trp Ile Lys Val
                65                  70                  75

GTC GCC ACC CGC AAC GCC CGC GAG CGC AGC ACC AGG CTC GAG AAC                                     381
Val Ala Thr Arg Asn Ala Arg Glu Arg Ser Thr Arg Leu Glu Asn
                80                  85                  90

ATG TGC TGG CGG ATC TGG CAC CTC GCG CGC AAG AAG AAG CAG CTG                                     426
Met Cys Trp Arg Ile Trp His Leu Ala Arg Lys Lys Lys Gln Leu
                95                  100                 105

GAG CTG GAG GGC ATC CAG AGA ATC TCG GCA AGA AGG AAG GAA CAG                                     471
Glu Leu Glu Gly Ile Gln Arg Ile Ser Ala Arg Arg Lys Glu Gln
                110                 115                 120

GAG CAG GTG CGT CGT GAG GCG ACG GAG GAC CTG GCC GAG GAT CTG                                     516
Glu Gln Val Arg Arg Glu Ala Thr Glu Asp Leu Ala Glu Asp Leu
                125                 130                 135

TCA GAA GGC GAG AAG GGA GAC ACC ATC GGA GAG CTT GCG CCG GTT                                     561
Ser Glu Gly Glu Lys Gly Asp Thr Ile Gly Glu Leu Ala Pro Val
                140                 145                 150

GAG ACG ACC AAG AAG AAG TTC CAG AGG AAC TTC TCT GAC CTT ACC                                     606
Glu Thr Thr Lys Lys Lys Phe Gln Arg Asn Phe Ser Asp Leu Thr
                155                 160                 165

GTC TGG TCT GAC GAC AAT AAG GAG AAG AAG CTT TAC ATT GTG CTC                                     651
Val Trp Ser Asp Asp Asn Lys Glu Lys Lys Leu Tyr Ile Val Leu
                170                 175                 180

ATC AGC GTG CAT GGT CTT GTT CGT GGA GAA AAC ATG GAA CTA GGT                                     696
Ile Ser Val His Gly Leu Val Arg Gly Glu Asn Met Glu Leu Gly
                185                 190                 195

CGT GAT TCT GAT ACA GGT GGC CAG GTG AAA TAT GTG GTC GAA CTT                                     741
Arg Asp Ser Asp Thr Gly Gly Gln Val Lys Tyr Val Val Glu Leu
                200                 205                 210

GCA AGA GCG ATG TCA ATG ATG CCT GGA GTG TAC AGG GTG GAC CTC                                     786
Ala Arg Ala Met Ser Met Met Pro Gly Val Tyr Arg Val Asp Leu
                215                 220                 225

TTC ACT CGT CAA GTG TCA TCT CCT GAC GTG GAC TGG AGC TAC GGT                                     831
Phe Thr Arg Gln Val Ser Ser Pro Asp Val Asp Trp Ser Tyr Gly
                230                 235                 240

GAG CCA ACC GAG ATG TTA TGC GCC GGT TCC AAT GAT GGA GAG GGG                                     876
Glu Pro Thr Glu Met Leu Cys Ala Gly Ser Asn Asp Gly Glu Gly
                245                 250                 255

ATG GGT GAG AGT GGC GGA GCC TAC ATT GTG CGC ATA CCG TGT GGG                                     921
Met Gly Glu Ser Gly Gly Ala Tyr Ile Val Arg Ile Pro Cys Gly
                260                 265                 270

CCG CGG GAT AAA TAC CTC AAG AAG GAA GCG TTG TGG CCT TAC CTC                                     966
Pro Arg Asp Lys Tyr Leu Lys Lys Glu Ala Leu Trp Pro Tyr Leu
                275                 280                 285

CAA GAG TTT GTC GAT GGA GCC CTT GCG CAT ATC CTG AAC ATG TCC                                    1011
Gln Glu Phe Val Asp Gly Ala Leu Ala His Ile Leu Asn Met Ser
```

```
                     290                 295                 300
AAG GCT CTG GGA GAG CAG GTT GGA ATT GGG AGG CCA GTA CTG CCT         1056
Lys Ala Leu Gly Glu Gln Val Gly Asn Gly Arg Pro Val Leu Pro
                305                 310                 315

TAC GTG ATA CAT GGG CAC TAT GCC GAT GCT GGA GAT GTT GCT GCT         1101
Tyr Val Ile His Gly His Tyr Ala Asp Ala Gly Asp Val Ala Ala
                320                 325                 330

CTC CTT TCT GGT GCG CTG AAT GTG CCA ATG GTG CTC ACT GGC CAC         1146
Leu Leu Ser Gly Ala Leu Asn Val Pro Met Val Leu Thr Gly His
                335                 340                 345

TCA CTT GGG AGG AAC AAG CTG GAA CAA CTG CTG AAG CAA GGG CGC         1191
Ser Leu Gly Arg Asn Lys Leu Glu Gln Leu Leu Lys Gln Gly Arg
                350                 355                 360

ATG TCC AAG GAG GAG ATC GAT TCG ACA TAC AAG ATC ATG AGG CGT         1236
Met Ser Lys Glu Glu Ile Asp Ser Thr Tyr Lys Ile Met Arg Arg
                365                 370                 375

ATC GAG GGT GAG GAG CTG GCC CTG GAT GCG TCA GAG CTT GTA ATC         1281
Ile Glu Gly Glu Glu Leu Ala Leu Asp Ala Ser Glu Leu Val Ile
                380                 385                 390

ACG AGC ACA AGG CAG GAG ATT GAT GAG CAG TGG GGA TTG TAC GAT         1326
Thr Ser Thr Arg Gln Glu Ile Asp Glu Gln Trp Gly Leu Tyr Asp
                395                 400                 405

GGA TTT GAT GTC AAG CTT GAG AAA GTG CTG AGG GCA CGG GCG AGG         1371
Gly Phe Asp Val Lys Leu Glu Lys Val Leu Arg Ala Arg Ala Arg
                410                 415                 420

CGC GGG GTT AGC TGC CAT GGT CGT TAC ATG CCT AGG ATG GTG GTG         1416
Arg Gly Val Ser Cys His Gly Arg Tyr Met Pro Arg Met Val Val
                425                 430                 435

ATT CCT CCG GGA ATG GAT TTC AGC AAT GTT GTA GTT CAT GAA GAC         1461
Ile Pro Pro Gly Met Asp Phe Ser Asn Val Val Val His Glu Asp
                440                 445                 450

ATT GAT GGG GAT GGT GAC GTC AAA GAT GAT ATC GTT GGT TTG GAG         1506
Ile Asp Gly Asp Gly Asp Val Lys Asp Asp Ile Val Gly Leu Glu
                455                 460                 465

GGT GCC TCA CCC AAG TCA ATG CCC CCA ATT TGG GCC GAA GTG ATG         1551
Gly Ala Ser Pro Lys Ser Met Pro Pro Ile Trp Ala Glu Val Met
                470                 475                 480

CGG TTC CTG ACC AAC CCT CAC AAG CCG ATG ATC CTG GCG TTA TCA         1596
Arg Phe Leu Thr Asn Pro His Lys Pro Met Ile Leu Ala Leu Ser
                485                 490                 495

AGA CCA GAC CCG AAG AAG AAC ATC ACT ACC CTC GTC AAA GCG TTT         1641
Arg Pro Asp Pro Lys Lys Asn Ile Thr Thr Leu Val Lys Ala Phe
                500                 505                 510

GGA GAG TGT CGT CCA CTC AGG GAA CTT GCA AAC CTT ACT CTG ATC         1686
Gly Glu Cys Arg Pro Leu Arg Glu Leu Ala Asn Leu Thr Leu Ile
                515                 520                 525

ATG GGT AAC AGA GAT GAC ATC GAC GAC ATG TCT GCT GGC AAT GCC         1731
Met Gly Asn Arg Asp Asp Ile Asp Asp Met Ser Ala Gly Asn Ala
                530                 535                 540

AGT GTC CTC ACC ACA GTT CTG AAG CTG ATT GAC AAG TAT GAT CTG         1776
Ser Val Leu Thr Thr Val Leu Lys Leu Ile Asp Lys Tyr Asp Leu
                545                 550                 555

TAC GGA AGC GTG GCG TTC CCT AAG CAT CAC AAT CAG GCT GAC GTC         1821
Tyr Gly Ser Val Ala Phe Pro Lys His His Asn Gln Ala Asp Val
                560                 565                 570

CCG GAG ATC TAT CGC CTC GCG GCC AAA ATG AAG GGC GTC TTC ATC         1866
Pro Glu Ile Tyr Arg Leu Ala Ala Lys Met Lys Gly Val Phe Ile
                575                 580                 585

AAC CCT GCT CTC GTT GAG CCG TTT GGT CTC ACC CTG ATC GAG GCT         1911
Asn Pro Ala Leu Val Glu Pro Phe Gly Leu Thr Leu Ile Glu Ala
```

-continued

```
              590                 595                 600
GCG GCA CAC GGA CTC CCG ATA GTC GCT ACC AAG AAT GGT GGT CCG         1956
Ala Ala His Gly Leu Pro Ile Val Ala Thr Lys Asn Gly Gly Pro
                605                 610                 615

GAC ATT ACA AAT GCA TTA AAC AAC GGA CTG CTC GTT GAC CCA CAC         2001
Val Asp Ile Thr Asn Ala Leu Asn Asn Gly Leu Leu Val Asp Pro
                620                 625                 630

GTC GAC CAG AAC GCC ATC GCT GAT GCA CTG CTG AAG CTT GTG GCA         2046
His Asp Gln Asn Ala Ile Ala Asp Ala Leu Leu Lys Leu Val Ala
                635                 640                 645

GAC AAG AAC CTG TGG CAG GAA TGC CGG AGA AAC GGG CTG CGC AAC         2091
Asp Lys Asn Leu Trp Gln Glu Cys Arg Arg Asn Gly Leu Arg Asn
                650                 655                 660

ATC CAC CTC TAC TCA TGG CCG GAG CAC TGC CGC ACT TAC CTC ACC         2136
Ile His Leu Tyr Ser Trp Pro Glu His Cys Arg Thr Tyr Leu Thr
                665                 670                 675

AGG GTG GCC GGG TGC CGG TTA AGG AAC CCG AGG TGG CTG AAG GAC         2181
Arg Val Ala Gly Cys Arg Leu Arg Asn Pro Arg Trp Leu Lys Asp
                680                 685                 690

ACA CCA GCA GAT GCC GGA GCC GAT GAG GAG GAG TTC CTG GAG GAT         2226
Thr Pro Ala Asp Ala Gly Ala Asp Glu Glu Glu Phe Leu Glu Asp
                695                 700                 705

TCC ATG GAC GCT CAG GAC CTG TCA CTC CGT CTG TCC ATC GAC GGT         2271
Ser Met Asp Ala Gln Asp Leu Ser Leu Arg Leu Ser Ile Asp Gly
                710                 715                 720

GAG AAG AGC TCG CTG AAC ACT AAC GAT CCA CTG TGG TTC GAC CCC         2316
Glu Lys Ser Ser Leu Asn Thr Asn Asp Pro Leu Trp Phe Asp Pro
                725                 730                 735

CAG GAT CAA GTG CAG AAG ATC ATG AAC AAC ATC AAG CAG TCG TCA         2361
Gln Asp Gln Val Gln Lys Ile Met Asn Asn Ile Lys Gln Ser Ser
                740                 745                 750

GCG CTT CCT CCG TCC ATG TCC TCA GTC GCA GCC GAG GGC ACA GGC         2406
Ala Leu Pro Pro Ser Met Ser Ser Val Ala Ala Glu Gly Thr Gly
                755                 760                 765

AGC ACC ATG AAC AAA TAC CCA CTC CTG CGC CGG CGC CGG CGC TTG         2451
Ser Thr Met Asn Lys Tyr Pro Leu Leu Arg Arg Arg Arg Arg Leu
                770                 775                 780

TTC GTC ATA GCT GTG GAC TGC TAC CAG GAC GAT GGC CGT GCT ASC         2496
Phe Val Ile Ala Val Asp Cys Tyr Gln Asp Asp Gly Arg Ala Ser
                785                 790                 795

AAG AAG ATG CTG CAG GTG ATC CAG GAA GTT TTC AGA GCA GTC CGA         2541
Lys Lys Met Leu Gln Val Ile Gln Glu Val Phe Arg Ala Val Arg
                800                 805                 810

GAC TCC CAG ATG TTC AAG ATC TCA GGG TTC ACG CTG TCG ACT GCC         2586
Ser Asp Ser Gln Met Phe Lys Ile Ser Gly Phe Thr Leu Ser Thr
                815                 820                 825

TCG ATG CCG TTG TCC GAG ACA CTC CAG CTT CTG CAG CTC GGC AAG         2631
Ala Met Pro Leu Ser Glu Thr Leu Gln Leu Leu Gln Leu Gly Lys
                830                 835                 840

ATC CCA GCG ACC GAC TTC GAC GCC CTC ATC TGT GGC AGC GGC AGC         2676
Ile Pro Ala Thr Asp Phe Asp Ala Leu Ile Cys Gly Ser Gly Ser
                845                 850                 855

GAG GTG TAC TAT CCT GGC ACG GCG AAC TGC ATG GAC GCT GAA GGA         2721
Glu Val Tyr Tyr Pro Gly Thr Ala Asn Cys Met Asp Ala Glu Gly
                860                 865                 870

AAG CTG CGC CCA GAT CAG GAC TAT CTG ATG CAC ATC AGC CAC CGC         2766
Lys Leu Arg Pro Asp Gln Asp Tyr Leu Met His Ile Ser His Arg
                875                 880                 885

TGG TCC CAT GAC GGC GCG AGG CAG ACC ATA GCG AAG CTC ATG GGC         2811
Trp Ser His Asp Gly Ala Arg Gln Thr Ile Ala Lys Leu Met Gly
```

```
                          890                895                900
GCT CAG GAC GGT TCA GGC GAC GCT GTC GAG CAG GAC GTG GCG TCC              2856
Ala Gln Asp Gly Ser Gly Asp Ala Val Glu Gln Asp Val Ala Ser
                          905                910                915

AGT AAT GCA CAC TGT GTC GCG TTC CTC ATC AAA GAC CCC CAA AAG              2901
Ser Asn Ala His Cys Val Ala Phe Leu Ile Lys Asp Pro Gln Lys
                          920                925                930

GTG AAA ACG GTC GAT GAG ATG AGG GAG CGG CTG AGG ATG CGT GGT              2946
Val Lys Thr Val Asp Glu Met Arg Glu Arg Leu Arg Met Arg Gly
                          935                940                945

CTC CGC TGC CAC ATC ATG TAC TGC AGG AAC TCG ACA AGG CTT CAG              2991
Leu Arg Cys His Ile Met Tyr Cys Arg Asn Ser Thr Arg Leu Gln
                          950                955                960

GTT GTC CCT CTG CTA GCA TCA AGG TCA CAG GCA CTC AGG TAT CTT              3036
Val Val Pro Leu Leu Ala Ser Arg Ser Gln Ala Leu Arg Tyr Leu
                          965                970                975

TCC GTG CGC TGG GGC GTA TCT GTG GGG AAC ATG TAT CTG ATC ACC              3081
Ser Val Arg Trp Gly Val Ser Val Gly Asn Met Tyr Leu Ile Thr
                          980                985                990

GGG GAA CAT GGC GAC ACC GAT CTA GAG GAG ATG CTA TCC GGG CTA              3126
Gly Glu His Gly Asp Thr Asp Leu Glu Glu Met Leu Ser Gly Leu
                          995                1000               1005

CAC ACC GTG ATC GTC CGT GGC GTC ACC GAG AAG GGT TCG GAA GCA              3171
His Lys Thr Val Ile Val Arg Gly Val Thr Glu Lys Gly Ser Glu
                          1010               1015               1020

CTG AAG GTG AGG AGC CCA GGA AGC TAC AAG AGG GAC GAT GTC GTC              3216
Ala Leu Val Arg Ser Pro Gly Ser Tyr Lys Arg Asp Asp Val Val
                          1025               1030               1035

CCG TCT GAG ACC CCC TTG GCT GCG TAC ACG ACT GGT GAG CTG AAG              3261
Pro Ser Glu Thr Pro Leu Ala Ala Tyr Thr Thr Gly Glu Leu Lys
                          1040               1045               1050

GCC GAC GAG ATC ATG CGG GCT CTG AAG CAA GTC TCC AAG ACT TCC              3306
Ala Asp Glu Ile Met Arg Ala Leu Lys Gln Val Ser Lys Thr Ser
                          1055               1060               1065

AGC GGC ATG                                                              3315
Ser Gly Met

TGAATTTGAT GCTTCTTTTA CATTTTGTCC TTTTCTTCAC TGCTATATAA                   3365

AATAAGTTGT GAACAGTACC GCGGGTGTGT ATATATATAT TGCAGTGACA                   3415

AATAAAACAG GACACTGCTA ACTATACTGG TGAATATACG ACTGTCAAGA                   3465

TTGTATGCTA AGTACTCCAT TTCTCAATGT ATCAATCGGA ATTC                         3509

(2) INFORMATION FOR SEQ ID NO: 13:

(i) SEQUENCE CHARACTERISTICS:
        (A) LENGTH: 33
        (B) TYPE: Nucleic acid
        (C) STRANDEDNESS: Unknown
        (D) TOPOLOGY: Unknown (ii) MOLECULE TYPE: cDNA (xi) SEQUENCE DESCRIPTION:SEQ ID NO: 13:

TCA ATG CCA CCA ATA TGG GCA GAA GTA ATG CGA                              33
Ser Met Pro Pro Ile Trp Ala Glu Val Met Arg
1               5                   10

(2) INFORMATION FOR SEQ ID NO: 14:

(i) SEQUENCE CHARACTERISTICS:
        (A) LENGTH: 33
        (B) TYPE: Nucleic acid
```

```
            (C) STRANDEDNESS:  Unknown
            (D) TOPOLOGY:  Unknown (ii) MOLECULE TYPE:  cDNA (xi) SEQUENCE DESCRIPTION:SEQ ID NO: 14:

AGC ATG CCC CCC ATC TGG GCC GAG GTC ATG AGC              33
Ser Met Pro Pro Ile Trp Ala Glu Val Met Arg
1               5                   10

(2) INFORMATION FOR SEQ ID NO: 15:

(i) SEQUENCE CHARACTERISTICS:
            (A) LENGTH:  33
            (B) TYPE:  Nucleic acid
            (C) STRANDEDNESS:  Unknown
            (D) TOPOLOGY:  Unknown (ii) MOLECULE TYPE:  cDNA (xi) SEQUENCE DESCRIPTION:SEQ ID NO: 15:

TCG ATG CCG CCG ATT TGG GCG GAA GTG ATG CGG              33
Ser Met Pro Pro Ile Trp Ala Glu Val Met Arg
1               5                   10

(2) INFORMATION FOR SEQ ID NO: 16:

(i) SEQUENCE CHARACTERISTICS:
            (A) LENGTH:  33
            (B) TYPE:  Nucleic acid
            (C) STRANDEDNESS:  Unknown
            (D) TOPOLOGY:  Unknown (ii) MOLECULE TYPE:  cDNA (xi) SEQUENCE DESCRIPTION:SEQ ID NO: 16:

TCT ATG CCT CCT ATA TGG GCT GAA GTT ATG CGT              33
Ser Met Pro Pro Ile Trp Ala Glu Val Met Arg
1               5                   10

(2) INFORMATION FOR SEQ ID NO: 17:

(i) SEQUENCE CHARACTERISTICS:
            (A) LENGTH:  42
            (B) TYPE:  Nucleic acid
            (C) STRANDEDNESS:  Unknown
            (D) TOPOLOGY:  Unknown (ii) MOLECULE TYPE:  cDNA (xi) SEQUENCE DESCRIPTION:SEQ ID NO: 17:

TTA AGA CCA GAC CAA GAC TAC TTA ATG CAC ATA AGA CAC AGA   42
Leu Arg Pro Asp Gln Asp Tyr Leu Met His Ile Ser His Arg
1               5                   10

(2) INFORMATION FOR SEQ ID NO: 18:

(i) SEQUENCE CHARACTERISTICS:
            (A) LENGTH:  42
            (B) TYPE:  Nucleic acid
            (C) STRANDEDNESS:  Unknown
            (D) TOPOLOGY:  Unknown (ii) MOLECULE TYPE:  cDNA (xi) SEQUENCE DESCRIPTION:SEQ ID NO: 18:

CTG CGC CCC GAT CAG GAT TAT CTG ATG CAT ATC TCC CAT CGC   42
Leu Arg Pro Asp Gln Asp Tyr Leu Met His Ile Ser His Arg
1               5                   10
```

-continued (2) INFORMATION FOR SEQ ID NO: 19:

(i) SEQUENCE CHARACTERISTICS:
        (A) LENGTH: 42
        (B) TYPE: Nucleic acid
        (C) STRANDEDNESS: Unknown
        (D) TOPOLOGY: Unknown (ii) MOLECULE TYPE: cDNA (xi) SEQUENCE DESCRIPTION:SEQ ID NO: 19:

```
TTC AGG CCG GAC CAA GAC TAC TTG ATG CAC ATT AGG CAC AGG          42
Leu Arg Pro Asp Gln Asp Tyr Leu Met His Ile Ser His Arg
1               5                   10
```

(2) INFORMATION FOR SEQ ID NO: 20:

(i) SEQUENCE CHARACTERISTICS:
        (A) LENGTH: 42
        (B) TYPE: Nucleic acid
        (C) STRANDEDNESS: Unknown
        (D) TOPOLOGY: Unknown (ii) MOLECULE TYPE: cDNA (xi) SEQUENCE DESCRIPTION:SEQ ID NO: 20:

```
TTT AGT CCT GAC CAA GAC TAC TTT ATG CAC ATA AGT CAC AGT          42
Leu Arg Pro Asp Gln Asp Tyr Leu Met His Ile Ser His Arg
1               5                   10
```

(2) INFORMATION FOR SEQ ID NO: 21:

(i) SEQUENCE CHARACTERISTICS:
        (A) LENGTH: 20
        (B) TYPE: Nucleic acid
        (C) STRANDEDNESS: Unknown
        (D) TOPOLOGY: Unknown (ii) MOLECULE TYPE: cDNA (ix) FEATURE:
        (D) OTHER INFORMATION: The N in positions 6, 9 and 18
            indicates inosine (xi) SEQUENCE DESCRIPTION:SEQ ID NO: 21:

```
ATGCCNCCNA TATGGGCNGA                                            20
```

(2) INFORMATION FOR SEQ ID NO: 22:

(i) SEQUENCE CHARACTERISTICS:
        (A) LENGTH: 20
        (B) TYPE: Nucleic acid
        (C) STRANDEDNESS: Unknown
        (D) TOPOLOGY: Unknown (ii) MOLECULE TYPE: cDNA (xi) SEQUENCE DESCRIPTION:SEQ ID NO: 22:

```
ATGCCCCCCA TCTGGGCCGA                                            20
```

(2) INFORMATION FOR SEQ ID NO: 23:

(i) SEQUENCE CHARACTERISTICS:
        (A) LENGTH: 20
        (B) TYPE: Nucleic acid
        (C) STRANDEDNESS: Unknown
        (D) TOPOLOGY: Unknown (ii) MOLECULE TYPE: cDNA (ix) FEATURE:
        (D) OTHER INFORMATION: The N in positions 6, 9 and 18 indicates inosine (xi) SEQUENCE DESCRIPTION:SEQ ID NO: 23:

ATGCCNCCNA TTTGGGCNGA                                              20

(2) INFORMATION FOR SEQ ID NO: 24:

(i) SEQUENCE CHARACTERISTICS:
        (A) LENGTH:  20
        (B) TYPE:  Nucleic acid
        (C) STRANDEDNESS:  Unknown
        (D) TOPOLOGY:  Unknown (ii) MOLECULE TYPE:  cDNA (ix) FEATURE:
        (D) OTHER INFORMATION:  The N in position 15
            indicates inosine (xi) SEQUENCE DESCRIPTION:SEQ ID NO: 24:

CTAGTCCTAA TAGANTACGT                                              20

(2) INFORMATION FOR SEQ ID NO: 25:

(i) SEQUENCE CHARACTERISTICS:
        (A) LENGTH:  20
        (B) TYPE:  Nucleic acid
        (C) STRANDEDNESS:  Unknown
        (D) TOPOLOGY:  Unknown (ii) MOLECULE TYPE:  cDNA (ix) FEATURE:
        (D) OTHER INFORMATION:  The N in position 15
            indicates inosine (xi) SEQUENCE DESCRIPTION:SEQ ID NO: 25:

CTGGTTCTGA TGGANTACGT                                              20

(2) INFORMATION FOR SEQ ID NO: 26:

(i) SEQUENCE CHARACTERISTICS:
        (A) LENGTH:  20
        (B) TYPE:  Nucleic acid
        (C) STRANDEDNESS:  Unknown
        (D) TOPOLOGY:  Unknown (ii) MOLECULE TYPE:  cDNA (ix) FEATURE:
        (D) OTHER INFORMATION:  The N in positions 6, 9
            and 18 indicates inosine (xi) SEQUENCE DESCRIPTION:SEQ ID NO: 26:

TACGGNGGNT AAACCCGNCT                                              20

(2) INFORMATION FOR SEQ ID NO: 27:

(i) SEQUENCE CHARACTERISTICS:
        (A) LENGTH:  20
        (B) TYPE:  Nucleic acid
        (C) STRANDEDNESS:  Unknown
        (D) TOPOLOGY:  Unknown (ii) MOLECULE TYPE:  cDNA (xi) SEQUENCE DESCRIPTION:SEQ ID NO: 27:

TACGGCGGCT AGACCCGCCT                                              20

(2) INFORMATION FOR SEQ ID NO: 28:

```
    (i) SEQUENCE CHARACTERISTICS:
        (A) LENGTH: 20
        (B) TYPE: Nucleic acid
        (C) STRANDEDNESS: Unknown
        (D) TOPOLOGY: Unknown (ii) MOLECULE TYPE: cDNA (ix) FEATURE:
        (D) OTHER INFORMATION: The N in positions 6 and 9
            indicates inosine (xi) SEQUENCE DESCRIPTION:SEQ ID NO: 28:

TACGGNGGNT ATACCCGCCT                                                   20

(2) INFORMATION FOR SEQ ID NO: 29:

(i) SEQUENCE CHARACTERISTICS:
        (A) LENGTH: 20
        (B) TYPE: Nucleic acid
        (C) STRANDEDNESS: Unknown
        (D) TOPOLOGY: Unknown (ii) MOLECULE TYPE: cDNA (ix) FEATURE:
        (D) OTHER INFORMATION: The N in position 15
            indicates inosine (xi) SEQUENCE DESCRIPTION:SEQ ID NO: 29:

GACCAAGACT ACCTNATGCA                                                   20

(2) INFORMATION FOR SEQ ID NO: 30:

(i) SEQUENCE CHARACTERISTICS:
        (A) LENGTH: 20
        (B) TYPE: Nucleic acid
        (C) STRANDEDNESS: Unknown
        (D) TOPOLOGY: Unknown (ii) MOLECULE TYPE: cDNA (xi) SEQUENCE DESCRIPTION:SEQ ID NO: 30:

GATCAGGATT ATCTCATGCA                                                   20

(2) INFORMATION FOR SEQ ID NO: 31:

(i) SEQUENCE CHARACTERISTICS:
        (A) LENGTH: 17
        (B) TYPE: Nucleic acid
        (C) STRANDEDNESS: Unknown
        (D) TOPOLOGY: Unknown (ii) MOLECULE TYPE: cDNA (ix) FEATURE:
        (D) OTHER INFORMATION: The N in positions 6 and 12
            indicates inosine (xi) SEQUENCE DESCRIPTION:SEQ ID NO: 31:

ACCCGNCTCC ANTACGC                                                      17

(2) INFORMATION FOR SEQ ID NO: 32:

(i) SEQUENCE CHARACTERISTICS:
        (A) LENGTH: 17
        (B) TYPE: Nucleic acid
        (C) STRANDEDNESS: Unknown
        (D) TOPOLOGY: Unknown (ii) MOLECULE TYPE: cDNA
```

(ix) FEATURE:
              (D) OTHER INFORMATION: The N in position 6
                  indicates inosine (xi) SEQUENCE DESCRIPTION:SEQ ID NO: 32:

ACCCGNCCTC ACTACTC                                                              17

(2) INFORMATION FOR SEQ ID NO: 33:

(i) SEQUENCE CHARACTERISTICS:
              (A) LENGTH: 17
              (B) TYPE: Nucleic acid
              (C) STRANDEDNESS: Unknown
              (D) TOPOLOGY: Unknown (ii) MOLECULE TYPE: cDNA (xi) SEQUENCE DESCRIPTION:SEQ ID NO: 33:

TACGTATAAT CAGTAGC                                                              17

(2) INFORMATION FOR SEQ ID NO: 34:

(i) SEQUENCE CHARACTERISTICS:
              (A) LENGTH: 17
              (B) TYPE: Nucleic acid
              (C) STRANDEDNESS: Unknown
              (D) TOPOLOGY: Unknown (ii) MOLECULE TYPE: cDNA (xi) SEQUENCE DESCRIPTION:SEQ ID NO: 34:

TACGTGTAGT CGGTGTC                                                              17

(2) INFORMATION FOR SEQ ID NO: 35:

(i) SEQUENCE CHARACTERISTICS:
              (A) LENGTH: 17
              (B) TYPE: Nucleic acid
              (C) STRANDEDNESS: Unknown
              (D) TOPOLOGY: Unknown (ii) MOLECULE TYPE: cDNA (xi) SEQUENCE DESCRIPTION:SEQ ID NO: 35:

TACGTATATT CAGTAGC                                                              17

(2) INFORMATION FOR SEQ ID NO: 36:

(i) SEQUENCE CHARACTERISTICS:
              (A) LENGTH: 14
              (B) TYPE: Nucleic acid
              (C) STRANDEDNESS: Unknown
              (D) TOPOLOGY: Unknown (ii) MOLECULE TYPE: cDNA (ix) FEATURE:
              (D) OTHER INFORMATION: The N in positions 3, 6 and 9
                  indicates inosine (xi) SEQUENCE DESCRIPTION:SEQ ID NO: 36:

AANGCNGGNC TAGT                                                                 14

(2) INFORMATION FOR SEQ ID NO: 37:

(i) SEQUENCE CHARACTERISTICS:
              (A) LENGTH: 14
              (B) TYPE: Nucleic acid
              (C) STRANDEDNESS: Unknown

```
        (D) TOPOLOGY:  Unknown (ii) MOLECULE TYPE:  cDNA (xi) SEQUENCE DESCRIPTION:SEQ ID NO: 37:

GACTCCGGCC TGGT                                                      14
```